(12) United States Patent
Seoane Suarez et al.

(10) Patent No.: US 8,926,956 B2
(45) Date of Patent: Jan. 6, 2015

(54) ANTIBODY RECOGNIZING HUMAN LEUKEMIA INHIBITORY FACTOR (LIF)

(75) Inventors: Joan Seoane Suarez, Barcelona (ES); Judit Anido Folgueira, Barcelona (ES); Andrea Saez Borderias, Barcelona (ES)

(73) Assignees: Fundacio Privada Institut d'Investigacio Oncologica Vall d'Hebron (VHIO), Barcelona (ES); Fundacio Privada Institucio Catalana de Recerca I Estudis Avancats (ICREA), Barcelona (ES)

( * ) Notice: Subject to any disclaimer, the term of this patent is extended or adjusted under 35 U.S.C. 154(b) by 0 days.

(21) Appl. No.: 13/261,464

(22) PCT Filed: Apr. 5, 2011

(86) PCT No.: PCT/EP2011/055253
§ 371 (c)(1),
(2), (4) Date: Feb. 13, 2013

(87) PCT Pub. No.: WO2011/124566
PCT Pub. Date: Oct. 13, 2011

(65) Prior Publication Data
US 2013/0142808 A1    Jun. 6, 2013

(30) Foreign Application Priority Data

Apr. 5, 2010    (EP) .................................... 10380049

(51) Int. Cl.
*C07K 16/24*    (2006.01)
*C12N 5/12*    (2006.01)
*A61K 39/395*    (2006.01)
*A61K 39/00*    (2006.01)

(52) U.S. Cl.
CPC ....... *A61K 39/39558* (2013.01); *C07K 2317/76* (2013.01); *C07K 16/248* (2013.01); *C07K 16/24* (2013.01); *A61K 2039/505* (2013.01)
USPC ...................... 424/85.1; 530/388.23; 435/326

(58) Field of Classification Search
CPC .......................... A61K 38/00; A61K 2039/505
USPC ...................... 424/85.1; 530/388.23; 435/326
See application file for complete search history.

(56) References Cited

FOREIGN PATENT DOCUMENTS

| CN | 101440128 A | 5/2009 |
| WO | WO 93/23556 A1 | 11/1993 |
| WO | WO 96/33740 A1 | 10/1996 |

OTHER PUBLICATIONS

Anido et al., "TFG-β Receptor Inhibitors Target the CD44$^{high}$/Id1$^{high}$ Glioma-Initiating Cell Population in Human Glioblastoma," Cancer Cell, Dec. 14, 2010, 18:655-668.

Decker et al., "CD44 Loss of Function in Spontaneous Murine Glioma Implicates CD44 in Tumor Maintenance," Neuro-Oncology, Oct. 1, 2009, 578:61.
Hirobe, Tomohisa, "Role of Leukemia Inhibitory Factor in the Regulation of the Proliferation and Differentiation of Neonatal Mouse Epidermal Melanocytes in Culture," Journal of Cellular Physiology, 2002, 192:315-326.
Huang et al., "Evaluation of CD44 as a Biomarker for Brain Tumor Prognosis," Neuro-Oncology, Oct. 31, 2009, 11(5):358.
Hudis, Clifford A., M.D., "Trastuzumab—Mechanism of Action and Use in Clinical Practice," The New England Journal of Medicine, Jul. 5, 2007, 357(1):39-51.
Kamohara et al., "Leukemia inhibitory factor functions as a growth factor in pancreas carcinoma cells: Involvement of regulation of LIF and its receptor expression," International Journal of Oncology, Apr. 2007, 30(4):977-983.
Kellokumpu-Lehtinen et al., "Leukemia-Inhibitory Factor Stimulates Breast, Kidney and Prostate Cancer Cell Proliferation by Paracrine and Autocrine Pathways," Int. J. Cancer, 1996, 66:515-519.
Kim et al., "Detection of human leukemia inhibitory factor by monoclonal antibody based ELISA," Journal of Immunological Methods, 1992, 156:9-17.
Peñuelas et al., "TGF-β Increases Glioma-Initiating Cell Self-Renewal through the Induction of LIF in Human Glioblastoma," Cancer Cell, Apr. 7, 2009, 15:315-327.
Ravandi et al., "The Role of Leukemia Inhibitory Factor in Cancer and Cancer Metastasis," Cancer Metastasis Biology and Treatment Growth Factors and Their Receptors in Cancer Metastasis, Jan. 1, 2004, 2:1-25.
Sengupta et al., "Monoclonal anti-leukemia inhibitory factor antibody inhibits blastocyst implantation in the rhesus monkey," Contraception, 2006, 74:419-425.
Soroceanu et al., "The Role of ID-1 in Modulating Brain Tumor Invasion and Dispersal," Neoru-Oncology, Oct. 31, 2009, 11(5):564:3.
Towle et al., "Deprivation of Leukemia Inhibitory Factor by Its Function-Blocking Antibodies Augments T Cell Activation," Journal of Interferon and Cytokine Research, 1998, 18:397-392.
Tsuchiya et al., "Targeting Id1 and Id3 inhibits peritoneal metastasis of gastric cancer," Cancer Sci., Nov. 2005, 96(11):784-790.
Godard et al., "Generation of monoclonal antibodies against HILDA/LIF and their use in the quantitative assay of the cytokine," Cytokine, Jan. 1, 1993, 5(1):16-23, XP023271369.

*Primary Examiner* — Prema Mertz
(74) *Attorney, Agent, or Firm* — Foley & Lardner LLP

(57) ABSTRACT

The invention relates to antibodies directed against human Leukemia Inhibitory Factor (LIF) and to a hybridoma cell line producing said antibodies. The invention also relates to a method for blocking/inhibiting the proliferation of stem cells, and to an in vitro method for the diagnosis of diseases associated with unwanted cell proliferation in a subject or for determining the predisposition of a subject to suffer from said disease associated with unwanted cell proliferation, or for prognosis of average life expectancy of a subject suffering from said disease. The therapeutic potential of said antibodies is based on observing that the inhibition of LIF can be used in therapeutic compositions for the treatment of diseases associated with unwanted proliferation.

10 Claims, 9 Drawing Sheets

A

B

ANTIBODY RECOGNIZING HUMAN LEUKEMIA INHIBITORY FACTOR (LIF)

CROSS-REFERENCE TO RELATED APPLICATIONS

This application is a National Stage application of PCT/EP2011/055253, filed Apr. 5, 2011, which claims priority from European Application No. 10380049.6, filed Apr. 5, 2010.

FIELD OF THE INVENTION

The present invention generally relates to a hybrid cell line (lymphocyte hybridoma) for the production of monoclonal antibodies recognizing human Leukemia Inhibitory factor (LIF), to a homogenous population of such antibodies, and to the use of such antibodies for the prognosis, diagnosis and treatment of diseases associated with altered levels or activity of LIF, such as of diseases associated with unwanted cell proliferation, more particularly, cancer, and even more particular, glioma.

STATE OF THE ART

Leukemia inhibitory factor (LIF) is an Interleukin 6 (IL-6)-type cytokine that is involved in a variety of biological activities and has effects on different cell types. Human LIF is a polypeptide of 202 amino acids.

LIF is an important signaling molecule; in particular, it plays a role in diseases associated with unwanted cell proliferation, such as various types of tumor. The self-renewal capacity of some tumor cells can be increased by the induction of LIF or Sox2 (Ikushima et al., Cell Stem Cell, 5:504-514, 2009; Penuelas et al., Cancer Cell, 15:315-327, 2009). LIF has also been implicated in other physiological activities, such as inhibition of blastocyst implantation (Sengupta et al., 2006, Contraception, 74, 419-425) and differentiation of epidermal melanocytes (Hirobe, 2002, J. Cell. Phys., 192:315-326)

In tumors, cancer initiating cells (CICs) are a cellular subpopulation that have characteristics of normal stem cells, exhibit sustained self-renewal and can generate secondary tumors that reproduce the characteristics and cellular diversity of the original tumor. CICs are considered to be responsible for tumor initiation, propagation, recurrence and chemo- and radioresistance (Bao et al., Nature, 444:7756-760, 2006; Dick, Blood, 112:4793-4807, 2008; Gupta et al., Nat. Mathods, 15:1010-1012, 2009; Visvader and Lindeman, Nat. Rev. Cancer, 8:755-768, 2008; Zhou et al., Nat. Rev. Drug Discov. 8:806-823, 2009). All these characteristics indicate that CICs are critical therapeutic targets and that the understanding of the biology of CICs is crucial to improve anti-cancer treatments. A number of cell surface markers, including CD133 and CD44, have proved useful for the isolation of subsets of cells enriched for CICs (Visvader and Lindeman, Nat. Rev. Cancer, 8:755-768, 2008) in different tumor types.

Glioma is the most common tumor of the brain. The most aggressive form of glioma, grade IV glioma, also called glioblastoma (GBM), is one of the deadliest cancers with a median survival of around 14 months (Stupp et al., N. Engl. J. Med., 352:987-996, 2005). Despite progress in understanding the molecular mechanisms involved in the genesis and progression of glioma, the prognosis and the treatment of this type of tumor continues to be ineffective. Glioma initiating cells (GICs) are characterized by their high oncogenic potential, their capacity for self-renewal and their capacity of differentiating into multiple cell lines. The number of stem cell-like cells in a tumor is regulated by its capacity of self-regeneration. GICs and, generally, cancer stem cells experience symmetric and asymmetric divisions by means of which a stem cell generates two identical copies thereof or a copy of the stem cell and a more differentiated cell (asymmetric division). The capacity of self-regeneration of the cancer stem cell is regulated by the balance between the symmetric and asymmetric divisions and the deregulation of the mechanisms controlling said self-renewal is most likely involved in the onset of the tumor.

It is considered that GICs are responsible for the onset, propagation and recurrence of tumors, indicating that the most effective therapies will come from therapies directed at compartmentalizing glioma stem cells. A tumor will not be eradicated if GICs are not eliminated.

The TGFβ (transforming growth factor β) signaling pathway is involved in regulating many cellular activities such as cellular proliferation and differentiation through regulation of target gene. The TGFβ family of cytokines comprises TGFβs themselves (e.g. TGFβ1, TGFβ2, TGFβ3), activins and bone morphogenic proteins. TGFβ family members act through activiating serine/threonine kinase receptors at the cell-surface, which triggers intracellular signaling pathways involving the downstream effector SMAD, which, upon activation, directly transfers to the nucleus and activates transcription. It was shown that TGFβ can increase the self-renewal capacity of GICs through the induction of LIF or Sox2 (Ikushima et al., Cell Stem Cell, 5:504-514, 2009; Penuelas et al., Cancer Cell, 15:315-327, 2009). The important role of TGFβ in cancer signaling (Massague, Cell, 134:215-230, 2008) has prompted the clinical development of anti-cancer strategies based on the design of inhibitory compounds against TGFβ (Seoane et al., Clin. Transl. Oncol., 10:14-19, 2008; Yingling et al., Nat. Rev. Drug Discov., 3:1011-1022, 2004). In glioma, elevated TGFβ activity confers poor prognosis in patients (Bruna et al., Cancer Cell, 11:147-160, 2007) and shows a diverse oncogenic response that includes the induction of angiogenesis, immunosuppression, cell invasion and cell proliferation (Bruna et al., Cancer Cell, 11:147-160, 2007; Rich, Front. Biosci. e245-260, 2003). TGFβ family members regulate the expression of Inhibitors of the DNA binding protein 1 (Id1). Inhibitors of the DNA binding proteins (Ids) are transcription factors that regulate cell cycle and cell differentiation and have an important role in the control of stem cell self-renewal (Perk et al., Nat. Rev. Cancer, 5:603-614, 2005; Ying et al., Cell, 115:281-292, 2003). In normal epithelial cells, TGFβ represses and BMP induces Id1 transcription (Massague, Cell, 134:215-230, 2008). However, in endothelial cells and some tumor cells, TGFβ is able to induce Id1 expression (Goumans et al., EMBO J., 1743-1753, 2002; Padua et al., Cell, 133:66-77, 2008). Id1 is expressed in B1 type adult neural stem cells having an important role in the regulation of the self-renewal capacity of these cells (Nam and Benezra, Cell Stem Cell, 5:515-526, 2009). In cancer, Id1 is found upregulated in several tumors (Perk et al., Cancer Res., 2006:10870-10877, 2006) and described to be involved in metastasis (Gupta et al., Proc. Natl. Acad. Sci. USA, 104:19506-19511, 2007).

The treatment of choice for glioma is surgical intervention. Nevertheless, surgical treatment is usually accompanied by a pharmacological adjuvant treatment or by means of radiotherapy. The drugs of choice for the treatment of glioma include the combination referred to as PCV which comprises procarbazine, CCNU (lomustine) and vincristine, temozolomide in combination with radiotherapy.

Therefore, it is necessary to have alternative treatments which prevent the drawbacks of treatments known in the state of the art and which can efficiently eliminate GICs.

Several antibodies specific to LIF are described in U.S. Pat. No. 5,654,157A, U.S. Pat. No. 5,654,157, Kim et al., (J. Immunol. Meth., 156: 9-17, 1992), Alphonso et al., (J. Leukocyte Biology (Abstracts of the 28th National Meeting of the Society for Leukocyte Biology, vol. 0, no. SP. 2 (1991) (NY, N.E., p. 49) (Mabs D4.16.9, D25.1.4, and D62.3.2), Sengupta et al., (Contraception 74:419-425, 2010). However, the antigenic regions within the LIF protein to which these antibodies bind, have not been characterized in detail. Furthermore, use of these antibodies for treatment of cancer, in particular glioma, and more particular, glioblastoma, has not been disclosed. As the skilled person will know from other examples in the art, the binding of an antibody to a particular region or epitope of the antigen can be decisive for the success of a therapy. For example, various anti-HER2 antibodies are known, of which only one, Trastuzumab, has been proven to be particularly useful for treatment of breast cancer.

SUMMARY OF THE INVENTION

In a first aspect, the invention relates to a monoclonal antibody directed against human leukemia inhibitory factor (LIF).

In another aspect, the invention relates to a hybridoma cell line producing a homogeneous population of antibodies directed against human leukemia inhibitory factor (LIF), hereinafter named anti-LIF antibody. In a particular embodiments thereof, the invention relates to the hybridoma cell line with the accession number DSM ACC3054, deposited on Apr. 1, 2010 at the Deutsche Sammlunf für Mikroorganismen and Zelljulturen GmbH located at Inhoffenstr, 7B, D-38124, Braunchweig, Germany.

In another aspect, the invention relates to immunoanalytical assays comprising said antibody.

In another aspect, the invention relates to a therapeutically effective amount of an anti-LIF antibody for the treatment of diseases associated with unwanted cell proliferation.

In a more particular aspect, the invention relates to a therapeutically effective amount of the monoclonal anti-LIF antibody in the sense of this invention for the treatment of diseases associated with unwanted cell proliferation.

In another aspect, the invention relates to a pharmaceutical composition comprising a therapeutically effective amount of said antibody according to the invention and a pharmaceutically acceptable carrier for the treatment of diseases associated with unwanted cell proliferation.

In another aspect, the invention relates to an in vitro method for the diagnosis of diseases associated with unwanted cell proliferation in a subject or for determining the predisposition of a subject to suffer from said disease associated with unwanted cell proliferation, or for determining the stage or severity of said disease associated with unwanted cell proliferation in a subject, or for monitoring the effect of the therapy administered to a subject with said disease associated with unwanted cell proliferation, which comprises quantifying the levels of LIF or of a functionally equivalent variant thereof or of any combination of these molecules in a biological sample from said subject. In another aspect, the invention relates to the use of a kit comprising reagents for the quantification of the expression levels of LIF or of a functionally equivalent variant thereof or of any combination of these molecules for the diagnosis of cancer in a subject or for determining the predisposition of a subject to suffer from said cancer, or for determining the stage or severity of said cancer in a subject, or for predicting the probability of survival or of the average expected life expectancy of a subject suffering from said cancer, or for monitoring the effect of the therapy administered to a subject with said cancer, in which if the reagents detect an increase in the expression of LIF or of a functionally equivalent variant thereof or of any combination of these molecules with respect to a control sample, then said subject can suffer from a disease associated with unwanted cell proliferation, or presents a greater predisposition to suffer from said disease associated with unwanted cell proliferation, or presents greater severity of said disease, or the administered therapy is not being effective.

In another aspect, the invention relates to an in vitro method for the prognosis of average life expectancy of patients suffering from diseases associated with unwanted cell proliferation, which comprises quantifying the levels of LIF or of a functionally equivalent variant thereof or of any combination of these molecules in a biological sample from said subject.

DRAWINGS

(A) Scheme showing LIF gene secondary structure and sequential deletions performed in the LIF-EGFP fusion protein. (B) 293T cells were transfected with the indicated constructs. After 48 hours cells were lysed and immunoprecipitated with 1 μg of anti-LIF antibody over night at 4° C. Then, protein A/G was added to the lysates and immunoprecipitates were eluted. LIF fragments were detected by immunoblot using an anti-EGFP antibody. (C) Scheme showing the anti-LIF antibody binding domain.

Figure 2:
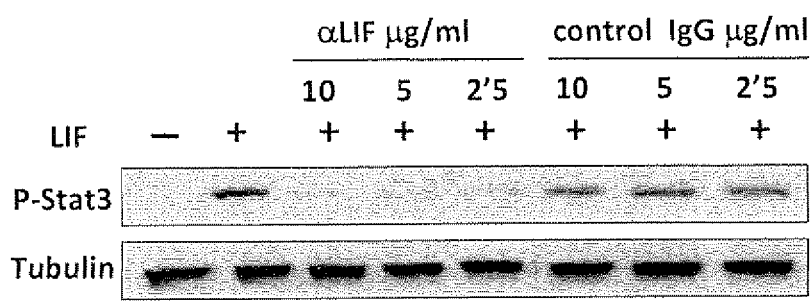
Figure 2:
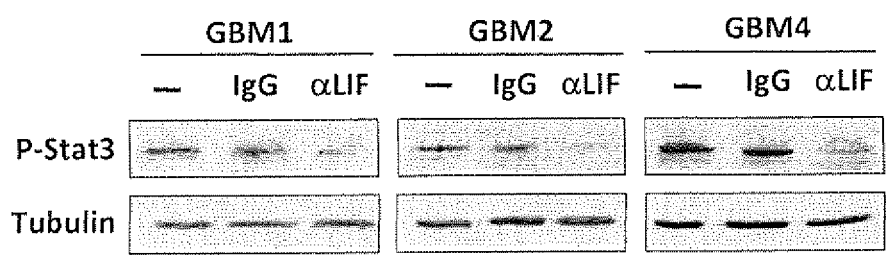

FIG. 2: anti-LIF antibody blocks the induction of Phospho-Stat3 by LIF in the glioma cell line U373 and the basal levels of Phospho-Stat3 in patient-derived GBM neurospheres.

A) U373 cells were treated with or without human recombinant LIF for 15 minutes in the presence or absence of the indicated monoclonal antibody and Phospho-Stat3 and tubulin levels were determined by Western Blot. Isotype-matched IgG were used as a control. B) GBM neurospheres were disgregated and either left untreated or incubated overnight in the presence of anti-LIF monoclonal antibody or isotype control IgG and the levels of Phospho-Stat3 and tubulin were determined by Western Blot.

Figure 3:
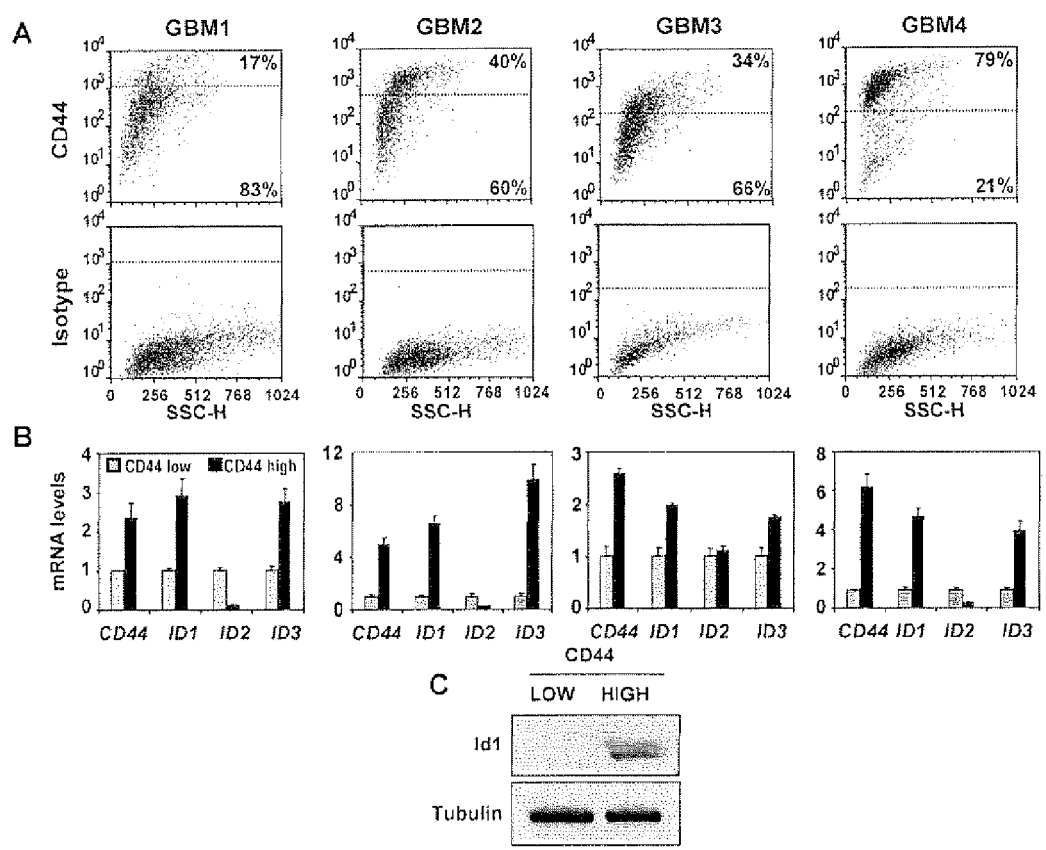

FIG. 3: Patient-derived GBM neurospheres contain a $CD44^{high}/Id1^{high}$ cell compartment.

FACS analysis of CD44 levels was performed in GBM neurospheres (FIG. 3A). Staining with isotype control is shown. GBM neurospheres were sorted by FACS according to CD44 levels and CD44, ID1, ID2 and ID3 transcript levels were determined by qRT-PCR and Western Blot analysis (FIGS. 3B and 3C).

Figure 4:
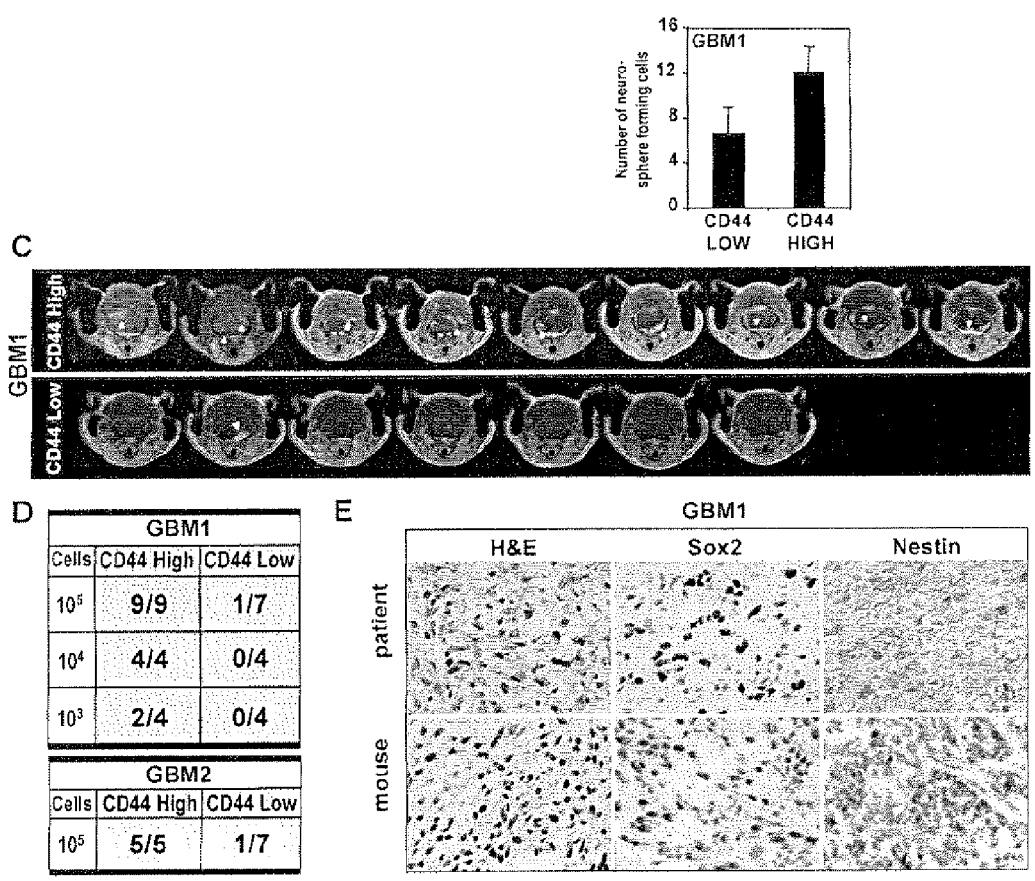

FIG. 4: The $CD44^{high}/Id1^{high}$ population in GBM neurospheres is enriched for glioma-initiating cells.

(A) FACS analysis of CD44 levels was performed in GBM1 neurospheres cultured in the presence or absence of 10% FBS for 10 days. (B) GBM1 cells were sorted according to CD44 levels and a neurosphere-forming assay was seeded. After 7 days, the number of neurospheres was determined. (C, D and E) Neurosphere cells were sorted according to CD44 levels and the indicated number of cells was inoculated in the brain of immunocompromised mice. (C) Forty days after surgery, images from the entire mouse brains inoculated with 10$^5$ cells were obtained by MRI (arrows indicate tumors). (D) Tumor incidence is shown. (E) Immunohistochemistry of the indicated proteins and H&E staining of the tumors were performed.

Figure 5:
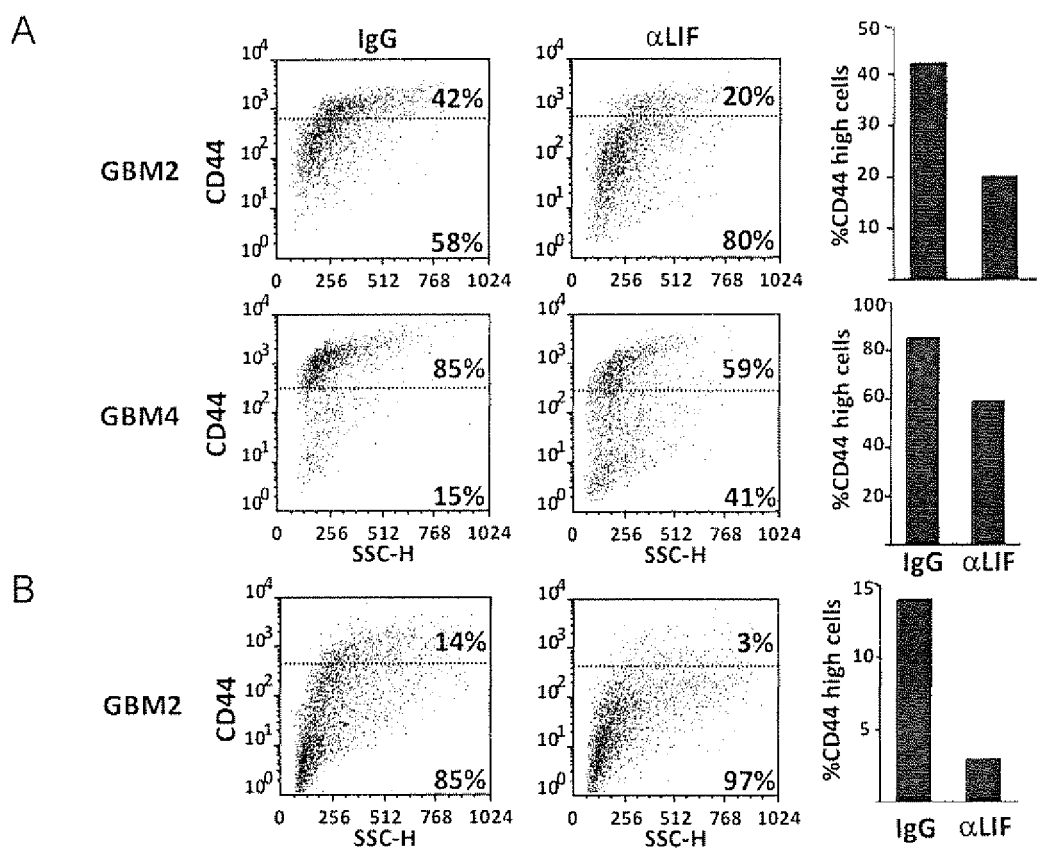

FIG. 5: anti-LIF antibody decreases the levels of the CD44$^{high}$/Id1$^{high}$ population in GBM neurospheres.

GBM neurospheres were dissociated and cultured in the presence of anti-LIF monoclonal antibody or isotype control IgG for 7 days either in the presence (A) or absence (B) of EGF and FGF. Cells were stained with anti-CD44-FITC monoclonal antibody in the presence of propidium iodide to exclude dead cells and the proportions of CD44 high cells were determined by FACS.

Figure 6:
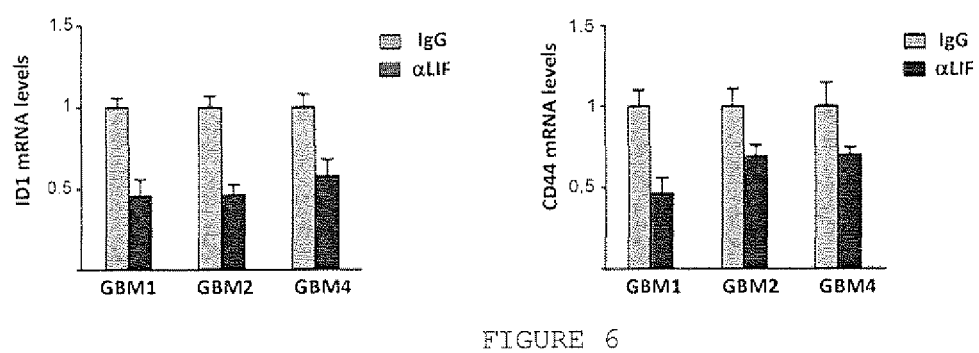

FIG. 6: anti-LIF antibody decreases the levels of the CD44 and Id1 in patient-derived GBM neurospheres.

GBM neurospheres were dissociated and cultured in the presence of anti-LIF monoclonal antibody or isotype control IgG for 7 days in the absence of EGF and FGF and mRNA levels of the indicated genes were analysed by qRT-PCR. GAPDH was used as an internal normalization control.

Figure 7:
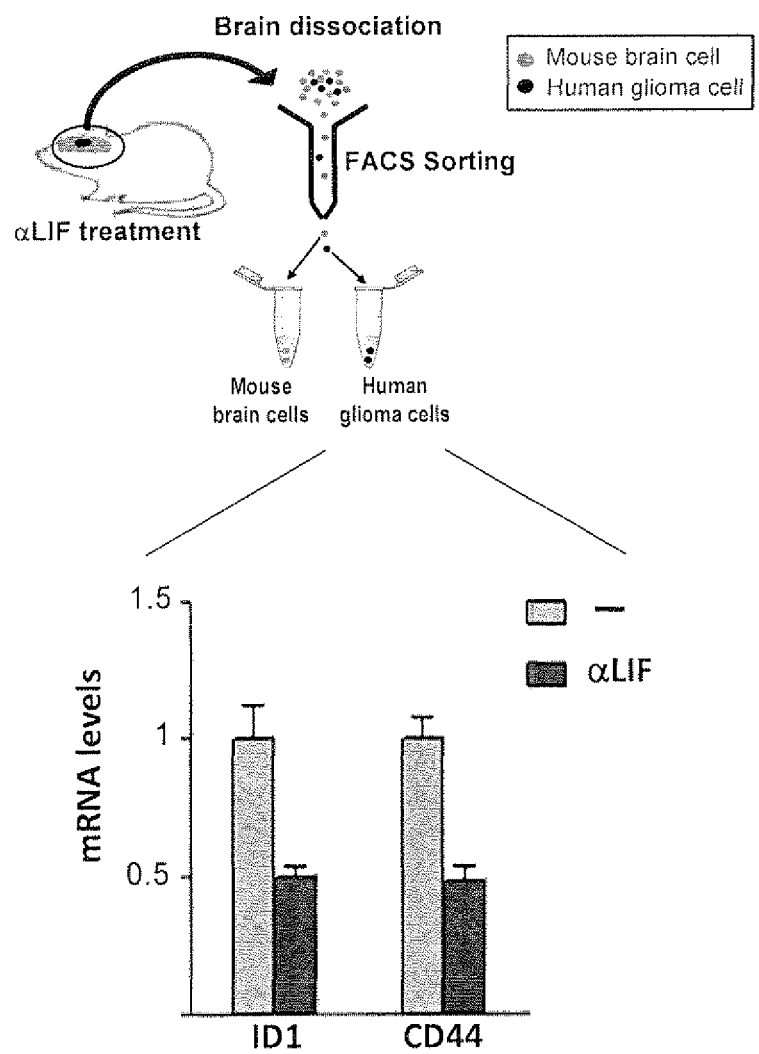

FIG. 7: In vivo treatment with anti-LIF antibody decreases the CD44$^{high}$/Id1$^{high}$ cell compartment.

(A) Scheme showing the experimental procedure. (B) GBM neurospheres were inoculated in the brain of immunocompromised mice. 30 days after inoculation a tumor was generated and when tumor formation was achieved mice were treated with PBS or 500 ug of anti-LIF monoclonal antibody every 3 days for 10 days. Mice brains were dissociated and human tumoral cells were isolated by sorting of MHC-I positive cells. The levels of ID1 and CD44 mRNA expression were determined by qRT-PCR. GAPDH was used as an internal normalization control.

Figure 8:
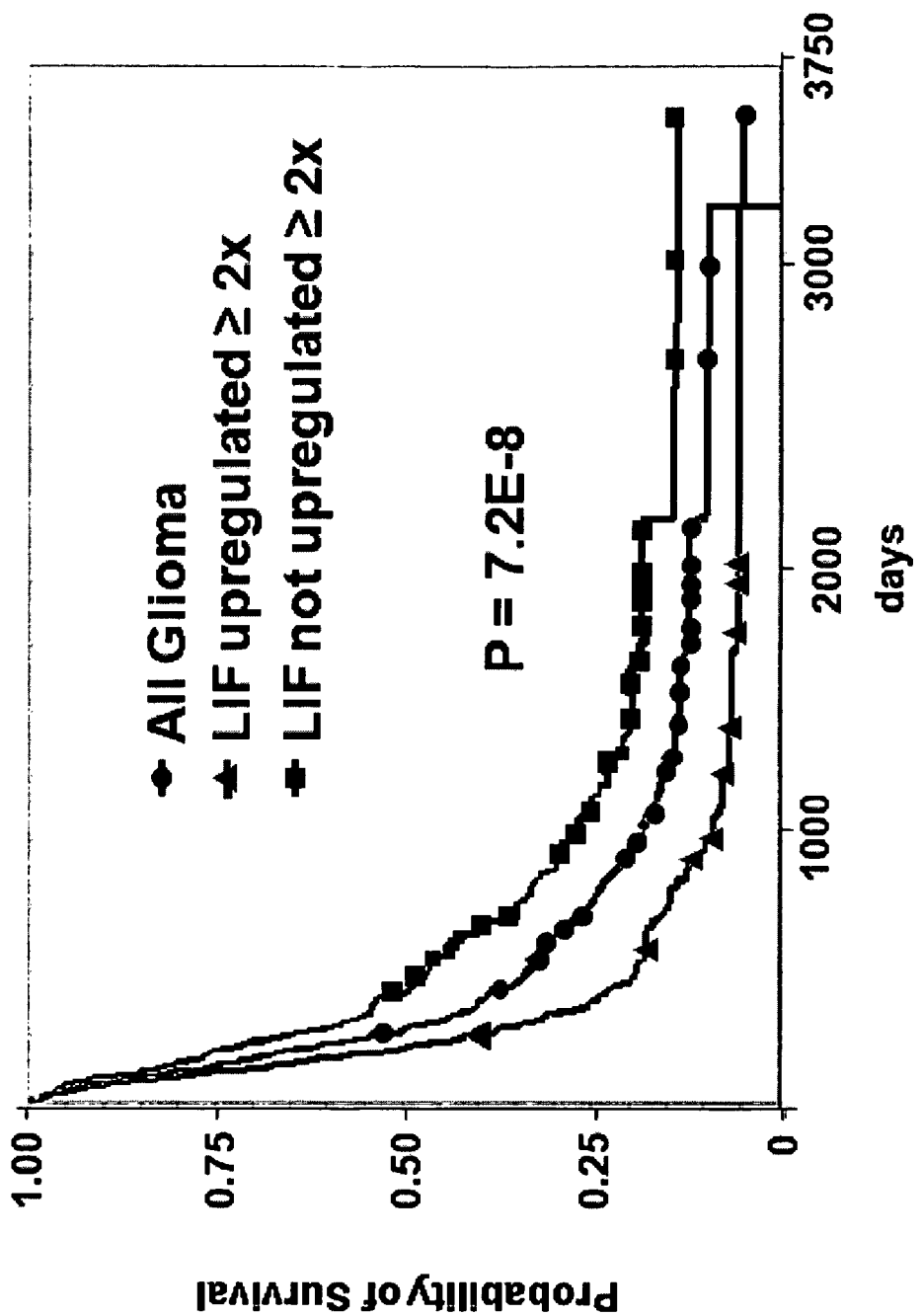

FIG. 8. LIF mRNA levels of glioma patients are linked to average life expectancy. Kaplan-Meier curves showing that the overall survival of glioma patients with LIF mRNA levels upregulated ≥2 fold is significantly lower than the rest of the patients (p=7.2E-8) by log-rank test. Data obtained from REpository for Molecular BRAin Neoplasia DaTa (REMBRANDT) program form the National Cancer Institute.

Figure 9:
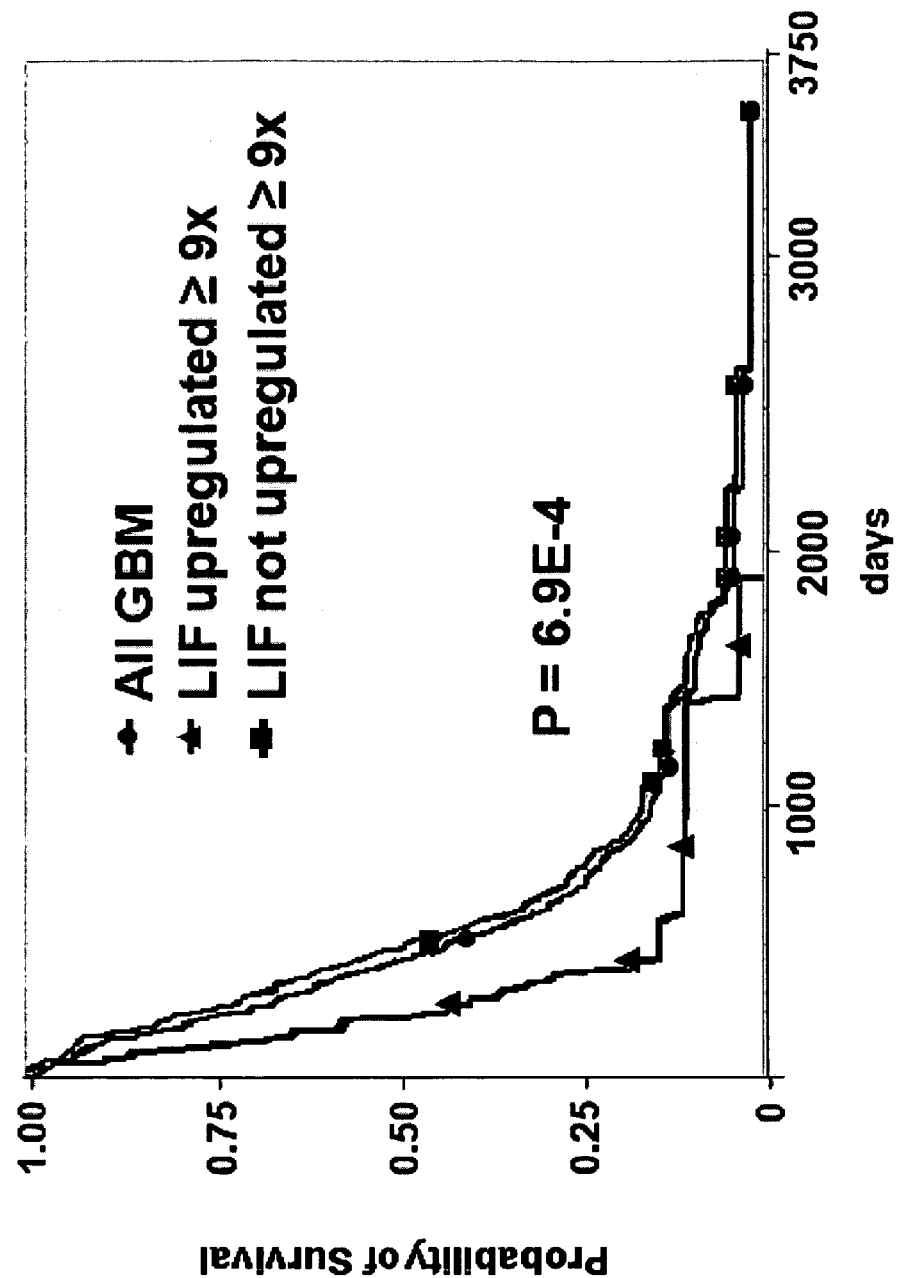

FIG. 9. LIF mRNA levels of glioblastoma (GEM) patients are linked to average life expectancy. Kaplan-Meier curves showing that the overall survival of GBM patients with LIF mRNA levels upregulated ≥9 fold is significantly lower than the rest of the patients (p=6.9E-4) by log-rank test. Data obtained from REpository for Molecular BRAin Neoplasia DaTa (REMBRANDT) program form the National Cancer Institute.

DETAILED DESCRIPTION OF THE INVENTION

Antibodies According to the Present Invention

The authors of the present invention have generated a novel monoclonal antibody directed against human Leukemia Inhibitory Factor (LIF).

Therefore, in a first aspect the invention relates to an antibody directed against human LIF which is monoclonal. The term "monoclonal antibody" as used herein refers to a substantially homogenous population of antibodies, where the individual antibody molecules comprising the population are essentially identical in affinity and specificity except for any possibly occurring natural mutations that may be present in minor amounts.

The monoclonal antibody is a homogenous population of antibodies specific for a single epitope of the antigen. In the present invention, the term "monoclonal antibody" must be interpreted broadly and it includes multispecific antibodies and fragments thereof (F(ab')2, Fab), etc. provided they are capable of specifically recognizing LIF. Fragments of the monoclonal antibody in the sense of the present invention, can, as non-limiting examples, be incorporated into recombinant antibodies, chimeric antibodies, humanized antibodies, human antibodies etc.

A chimeric antibody is a monoclonal antibody constructed by means of the cloning or recombination of antibodies from different animal species. In a typical but non-limiting configuration of the invention, the chimeric antibody includes part of the monoclonal antibody in the sense of this invention, generally the variable fragment (Fv) including the sites for antigen recognition and binding, and the other part corresponding to a human antibody, generally the part including the constant region and the adjacent constant region.

A humanized antibody is a monoclonal antibody constructed by means of the cloning and grafting of the hypervariable complementarity determining regions (CDR) of the murine monoclonal antibody in the sense of this invention into a human antibody in replacement of the hypervariable CDR regions of said human antibody.

A "human antibody" as used herein can mean a fully human monoclonal antibody. Such a human antibody is an antibody which may be produced by genetically engineered mice, so called transgenic mice, which had been modified to produce human antibodies. A technique for obtaining human antibodies from mice is for example described by Lonberg and Huszar (Int. Rev. Immunol., 1995; 13(1):65-93), based on a technology first described by McCafferty et al. (1990, Nature 348 (6301): 552-554).

In addition, in the context of the present invention, the term "antibody" also includes variants with an altered glycosylation pattern, as well as glycosylated or non-glycosylated antibody fragments, obtained from the protein or by means of recombinant technology, which can consist of (i) variable zones of the antibodies bound to one another by a binding peptide (scFv), (ii) the variable zone together with the CH1 constant of the heavy chain (Fd) bound to the light chain by means of cysteines or by means of binding peptides and disulfide bond (scFab), (iii) new variants, such as single heavy chains, or (iv) any modification made to the antibody fragments for the purpose of making them more similar, less immunogenic (humanized) or more stable in biological fluids and which in the context of the present invention, have the capacity to prevent LIF from performing its function (activity), i.e., inducing the activation of the JAK-STAT signaling pathway.

As the person skilled in the art will understand, the variants of the antibody in the sense of this invention can be obtained by means of conventional genetic engineering or recombinant techniques, antibody production techniques, techniques for extraction and purification from biological fluids or tissues, or by any other conventional technique for obtaining proteins and antibodies which are widely known by the person skilled in the art. Illustrative non-limiting examples of techniques are: by means of genetic engineering techniques they could be redesigned and expressed in vectors designed for the production of recombinant antibodies of different sizes, composition and structure. A review of the main methods for the production and purification of antibodies can be found, for example, in:

"Handbook of Therapeutic Antibodies", by S. Dübel. Editor: Wiley-VCH, 2007, Vol: I to III (ISBN 978-3527314539);

"Antibodies: Volume 1: Production and Purification" by G. Subramanian Ed., Editor: Springer, 1st Ed, 2004 (ISBN 978-0306482458);

"Antibodies: Volume 2: Novel Technologies and Therapeutic Use", by G. Subramanian Ed., Editor: Springer, first edition, 2004 (ISBN 978-0306483158);

"Molecular Cloning: a Laboratory manual", by J. Sambrook and D. W. Russel Eds., Publisher: Cold Spring Harbor Laboratory Press, third edition, 2001 (ISBN 978-0879695774).

In a particular embodiment, the invention relates to an antibody that recognizes full length human LIF, but does not recognize a LIF fragment corresponding to amino acids 1 to 72, and more preferably, does not recognize a LIF fragment corresponding to amino acids 1 to 127, and even more preferably, does not recognize a LIF fragment corresponding to amino acids 1 to 160.

Figure 1:
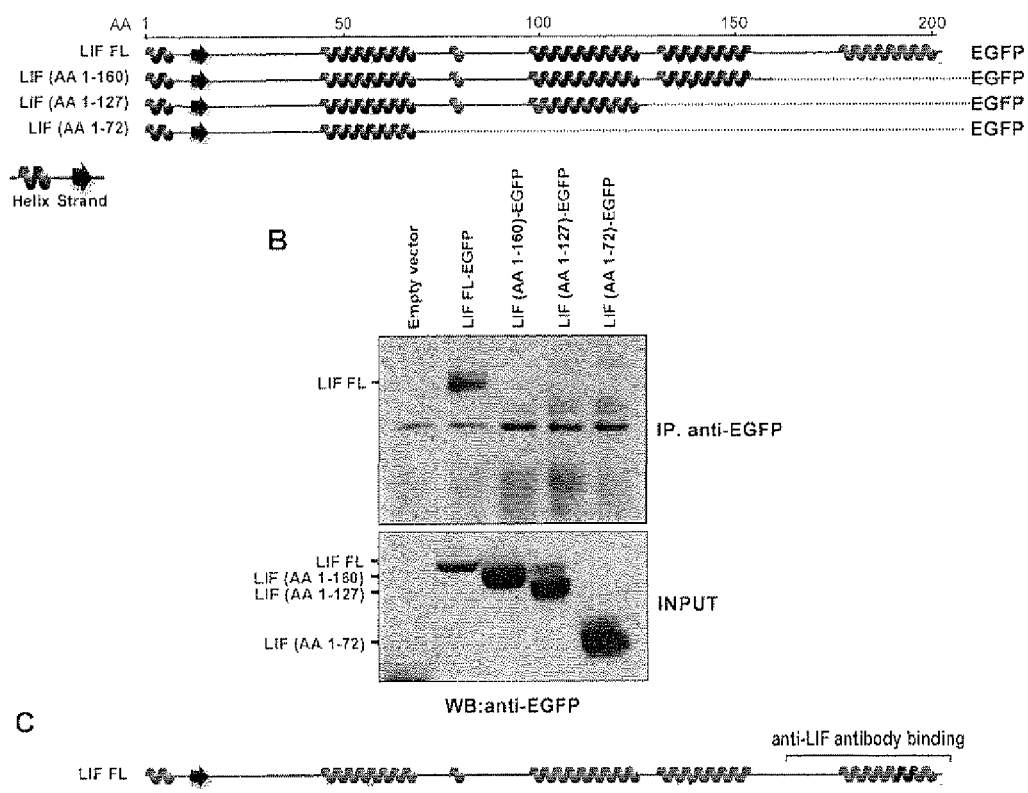
FIG. 1: anti-LIF antibody (α-LIF) binds to the C-terminal domain of the human LIF protein comprised in amino acids 160 to 202.

In the sense of the current invention, the region comprised by amino acids 160 to 202 of human LIF is required for recognition of LIF or a fragment thereof by said monoclonal antibody (FIG. 1). Therefore, in a particular embodiment, the invention relates to an antibody that recognizes an epitope within the region comprised by amino acids 160 to 202 of human LIF.

In an even more particular embodiment, said antibody recognizes an epitope comprised in the regions selected from the following: a region corresponding to amino acids 160 to 180, a region corresponding to amino acids 170 to 190, a region corresponding to amino acids 180 to 200, a region corresponding to amino acids 182 to 202 of human LIF.

The authors of the present invention have generated a hybridoma cell line producing an antibody that recognizes human LIF. Said antibody is of the IgG 1 isotype. This antibody recognizes a LIF fragment not comprised in the stretch of amino acid residues 1 to 160. Therefore, in another embodiment, the invention relates to a hybridoma cell line producing said antibody. A hybridoma cell line with the accession number DSM ACC3054, producing such an antibody has been deposited on Apr. 1, 2010 by Vall d'Hebron Institute of Oncology at the Deutsche Sammlung von Mikroorganismen and Zellkulturen GmbH. The hybridoma cell line with the accession number DSM ACC3054 is therefore comprised in this invention. This hybridoma cell line is also described in the European Patent Application 10 380 049.6.

As the person skilled in the art will understand, antibodies which bind to overlapping or partially overlapping epitopes of the antigen compete with each other for binding to the antigen. The skilled person will also understand that two essentially identical antibody molecules, such as two monoclonal antibody molecules produced by the same hybridoma cell line, will competitively inhibit each other's binding to the epitope of the antigen. Hence, by means of example, the binding of one antibody molecule produced by the hybridoma cell line DSM ACC3054 of this invention competitively inhibits the binding of any other individual antibody molecule produced by the same cell line to human LIF. It will also competitively inhibit the binding of any other antibody molecule from another source than DSM ACC3054, as long as the other antibody molecule is generally capable of binding to the same or to an overlapping epitope. The present inventors have characterized the region of LIF containing the epitope. Therefore, any antibody that is competitively inhibited in its binding to human LIF by the antibody defined above, is also an antibody according to this invention. In particular, any antibody that is competitively inhibited in its binding to human LIF by the antibody produced by the hybridoma cell line with the accession number DSM ACC3054, deposited on Apr. 1, 2010 by Vall d'Hebron Institute of Oncology at the Deutsche Sammlung von Mikroorganismen and Zellkulturen GmbH, is also considered an antibody according to this invention.

In another embodiment, the invention relates to the use of said antibody in an immoanalytical method, such as Western blot, immunohistochemistry or ELISA.

Therapeutic Methods of the Invention

The invention discerns the molecular mechanisms underlying the effect of anti-LIF antibodies, preferably anti-LIF antibodies according to the present invention, in human patients suffering from a disease associated with unwanted cell proliferation.

In the context of the present invention, a "disease associated with unwanted cell proliferation" includes the growth, progression and the metastasis of cancer and tumors. Examples of diseases associated with unwanted cell proliferation which can be treated according to the methods described in the present invention are cancer, restenosis, arteriosclerosis, angiogenic diseases, fibrosis, dermatological diseases such as psoriasis and inflammatory diseases.

In a particular embodiment of the invention, the disease associated with unwanted cell proliferation is cancer. This embodiment is preferred.

The terms "cancer" and "tumor" relate to the physiological condition in mammals characterized by the deregulated cell growth. Cancer is a class of diseases in which a group of cells display uncontrolled growth or unwanted growth. The uncontrolled growth can cause that these cells can invade, intrude and even destroy adjacent tissues. Cancer cells can also spread to other locations, which can lead to the formation of metastases. Spreading of cancer cells in the body can, for example, occur via lymph or blood. Uncontrolled growth, intrusion and metastasis formation are also termed malignant properties of cancers. The malignant properties differentiate cancers from benign tumors, which typically do not invade or metastasize. The compounds of the present invention are—without limitation thereto—useful for the treatment of cancers selected from the group of breast, heart, lung, small intestine, colon, spleen, kidney, bladder, head, neck, ovarian, prostate, brain, pancreatic, skin, bone, bone marrow, blood, thymus, uterine, testicular and liver tumors. Particularly, tumors which can be treated with the compounds of the invention include adenoma, adenocarcinoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and teratoma. Particularly, the tumor/cancer is selected from the group of acral lentiginous melanoma, actinic keratosis, adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, chondrosarcoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, gastronoma, germ line tumors, glioblastoma, glucagonoma, hemangioblastoma, hemangioendothelioma, hemangioma, hepatic adenoma, hepatic adenomatosis, hepatocellular carcinoma, insulinite, intraepithelial neoplasia, intraepithelial squamous cell neoplasia, invasive squamous cell carcinoma, large cell carcinoma, liposarcoma, lung carcinoma, lymphoblastic leukemia, lymphocytic leukemia, leiomyosarcoma, melanoma, malignant melanoma, malignant mesothelial tumor, nerve sheath tumor, medulloblastoma, medulloepithelioma, mesothelioma, mucoepidermoid carcinoma, myeloid leukemia, neuroblastoma, neuroepithelial adenocarcinoma, nodular melanoma, osteosarcoma, ovarian carcinoma, papillary serous adenocarcinoma, pituitary tumors, plasmacytoma, pseudosarcoma, prostate carcinoma, pulmonary blastoma, renal cell carcinoma, retinoblastoma, rhabdomyosarcoma, sarcoma, serous carcinoma, squamous cell carcinoma, small cell carcinoma, soft tissue carcinoma, somatostatin secreting tumor, squamous carcinoma, squamous cell carcinoma, undifferentiated carcinoma, uveal melanoma, verrucous carcinoma, vagina/vulva carcinoma, VIPpoma, Wilm's tumor. Even more preferably, the tumor/cancer to be treated with the compounds of the invention includes brain cancer, head and neck cancer, colorectal carcinoma, acute myeloid leukemia, pre-B-cell acute lymphoblastic leukemia, bladder cancer, astrocytoma, preferably grade II, III or IV astrocytoma, glioblastoma, preferably glioblastoma multiforme, small cell cancer, and non-small cell cancer, preferably non-small cell lung cancer, lung adenocarcinoma, metastatic melanoma, androgen-independent metastatic prostate cancer, androgen-dependent metastatic prostate cancer, prostate adenocarcinoma, and breast cancer, preferably breast ductal cancer or breast carcinoma.

In a particular embodiment, the cancer is one of the following: glioma, pre-B cell acute lymphoblastic leukemia, acute myeloid leukemia, colorectal carcinoma, lung adenocarcinoma, prostate adenocarcinoma, bladder cancer, breast ductal cancer or breast carcinoma. Even more preferably, said glioma is grade IV glioma.

TGFβ can induce the self-renewal capacity of cancer stem cells through the Smad-dependent induction of LIF. LIF, in return, is involved in the activation of the JAK-STAT pathway, thus inducing the cell proliferation process and the increase of tumor stem cells (cancer stem cells) (Penuelas et al., Cancer Cell, 15:315-327, 2009). Activation of STAT family members, such as Stat 3, typically occurs through their phosphorylation.

As expressed at the beginning of the description, the inventors have opened a new therapeutic window in the treatment of diseases associated with unwanted cell proliferation, such as cancer, especially for the treatment of cancer associated with high levels of LIF or of functionally equivalent variants thereof, with the invention herein described. Without wishing to be bound by any theory, it is thought that the effect of LIF and of its inhibitors on the proliferation of tumors lies in the capacity of LIF to promote the proliferation of tumor stem cells. The authors show that treatment with anti-LIF antibodies, preferably anti-LIF antibodies according to the present invention, reduces the LIF-dependent phosphorylation of Stat3 in cell culture (FIG. 2). Anti-LIF inhibitory antibodies are capable of inhibiting the proliferation of tumor stem cells, such that their use is particularly useful for the treatment of diseases that can benefit from inhibition of the proliferation of stem cells. As described above, the antibodies of the present invention have the property of recognizing a LIF fragment not comprised in the region comprising amino acid residues to 1 to 160 of human LIF, which means in return that these antibodies bind in the C-terminal segment of LIF. The present inventors have shown that, surprisingly, the antibodies having this property are particularly useful for the treatment of said diseases, including cancer (FIG. 2, FIG. 6).

Therefore, in another aspect, the invention relates to inhibitory antibodies for the treatment of diseases associated with unwanted cell proliferation, such as cancer for example, and especially for the treatment of cancer associated with high activity of LIF.

The term "Inhibitory antibody" is understood in the context of the present invention as an antibody which is capable of binding to LIF, thereby preventing LIF from being able to perform its functions. "Neutralizing antibody" is synonymous.

In breast cancer, a link between TGFβ and a cell population characterized by high levels of the cell surface marker CD 44 ($CD44^{high}$ population) has been described. TGFβ has been shown to increase the $CD44^{high}$ cell population enriched for CICs through the induction of an epithelial-mesenchymal transition (EMT) (Gupta et al., Cell, 138, 645-659, 2009; Mani et al., Cell, 133:504-715, 2008). However, in glioma, the $CD44^{high}$ compartment has not been extensively studied. The present invention identifies Id1 and CD44 as novel markers of cancer stem cells in glioma, more specifically glioblastoma (FIG. 3). In particular, the authors show that the $CD44^{high}/CD44^{high}$ cell population is enriched in glioma-initiating cells (GICs, FIG. 4).

In a non-limiting and merely illustrative example, the anti-LIF antibodies, preferably anti-LIF antibodies according to the present invention, target a cell population characterized by the expression of CD44 and Id1, which is enriched for glioma initiating cells (GICs). In particular, the anti-LIF antibodies, preferably anti-LIF antibodies according to the present invention, target the $CD44^{high}/Id1^{high}$ GICs through the repression of Id1 and Id3 (FIG. 5). Moreover, the antibodies are capable of depleting the $CD44^{high}/Id1^{high}$ GIC population. Hence, the authors of the present invention have found that anti-LIF antibodies, preferably anti-LIF antibodies according to the present invention, function as inhibitors of the pathway regulated by transforming growth factor beta (TGFβ) family members. Therefore, in a particular embodiment, the present invention relates to the antibody or fragment thereof or pharmaceutical composition of the invention, wherein said antibody or fragment thereof or pharmaceutical composition is capable of reducing the cell population characterized by high levels of CD 44 and Id1. An illustrative example thereof is shown in FIG. 5. GBM neurospheres are a preferred example of the cell population characterized by high levels of CD 44 and Id1. For example, in glioblastoma-patient derived cell lines, anti-LIF antibodies, preferably anti-LIF antibodies according to the present invention, reduce the expression levels of Id1 and CD44 (FIG. 6).

Furthermore, the authors show that in vivo treatment with anti-LIF antibodies, preferably anti-LIE antibodies according to the present invention, decreases the $CD44^{high}/Id1^{high}$ cell compartment (FIG. 7). Therefore, administering of anti-LIF antibodies, preferably anti-LIF antibodies according to the present invention, can prevent tumor initiation and is believed to prevent tumor recurrence.

In a particular embodiment of the invention, the cancer or the cells forming the tumors occurring in the cancer is characterized by presenting high levels of LIF. In the context of the present invention, with "high levels" of LIF, it is understood that the concentrations of LIF are greater than those occurring in a control sample by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150% or more.

Control sample is understood as a sample having levels of LIF which are used as a reference for the determination of the relative levels of LIF in a test sample. The reference samples are typically obtained from patients who are well documented from the clinical point of view, and who present no disease. In said samples, the biomarker concentration can be determined, for example, by means of the determination of the average concentration in a reference population. In the determination of the reference concentration for a certain marker, it is necessary to take into consideration some characteristics of the type of sample, such as age, gender, the physical state and the like of the patient. For example, the reference sample can be obtained from identical amounts of a group of at least 2, at least 10, at least 100 to more than 1000 individuals, such that the population is statistically significant.

The concentration of LIF can be determined intracellular, in the interstitial gap or in extracts in which both the intracellular protein and the one found in the interstitial gap. The levels of LIF can be determined by means of measuring the amount of protein using immunological methods.

In a more particular embodiment, the immunological method for determination of LIF levels comprises an anti-LIF antibody, and in an even more particular embodiment, it comprises the antibody according to the present invention.

In another aspect, the invention relates to a pharmaceutical composition comprising a therapeutically effective amount of an inhibitory agent according to the present invention together with a pharmaceutically acceptable carrier for the treatment of diseases associated with unwanted cell proliferation. Examples of diseases associated with unwanted cell proliferation have been mentioned above in the specification.

In the context of the present invention, "therapeutically effective amount" is understood as the amount of agent inhibiting the expression and/or activity of LIF that is necessary to achieve the desired effect which, in this specific case, is the treatment of diseases associated with unwanted cell proliferation. Generally, the therapeutically effective amount of the antibody according to the present invention to be administered will depend, among other factors, on the individual to be treated, on the severity of the disease said individual suffers, on the chosen dosage form, etc. For this reason, the doses mentioned in this invention must be considered only as a guideline for the person skilled in the art, and the latter must adjust the doses according to the previously mentioned variables. Nevertheless, the antibody according to the present invention can be administered one or more times a day, for example, 1, 2, 3 or 4 times a day.

In the context of this specification, the term "treatment" or "treating" means the administration of an antibody according to the invention to prevent, relieve or eliminate the disease or one or more symptoms associated with said disease associated with unwanted cell proliferation. "Treatment" also includes preventing, relieving or eliminating the physiological sequelae of the disease. In the context of this invention, the term "relieve" is understood to mean any improvement of the situation of the treated patient—both subjectively (feelings of or about the patient) and objectively (measured parameters).

The term "vehicle, adjuvant and/or carrier" relates to molecular entities or substances with which the active ingredient is administered. Such pharmaceutical vehicles, adjuvants or carriers can be sterile liquids, such as waters and oils, including those of petroleum or of an animal, plant or synthetic origin, such as peanut oil, soybean oil, mineral oil, sesame oil and the like, excipients, disintegrating agents, wetting agents or diluents. Suitable pharmaceutical carriers are described in "Remington's Pharmaceutical Sciences" by E. W. Martin.

In the context of the present invention, the term "pharmaceutically acceptable" relates to molecular entities and compositions which are physiologically tolerable and do not typically cause an allergic reaction or a similar adverse reaction, such as gastric disorder, dizziness and the like, when they are administered to a human. The term "pharmaceutically acceptable" preferably means approved by a federal or state government regulatory agency, or included in the US Pharmacopoeia or other generally recognized pharmacopoeia for use in animals, and more particularly in humans.

The antibody, as well as the pharmaceutical compositions containing said antibody, can be used together with other additional drugs useful in the treatment of diseases associated with unwanted cell proliferation. Said additional drugs can form part of the same pharmaceutical composition or they can alternatively be provided in the form of a separate composition for their administration that may or may not be simultaneous to that of the pharmaceutical composition comprising said antibody.

Examples of other additional drugs useful in the treatment of diseases associated with unwanted cell proliferation include but are not limited to alkylating agents such as, for example, cyclophosphamide, carmustine, daunorubicin, mechlorethamine, chlorambucil, nimustine, melphalan and the like; anthracyclines, such as, for example, daunorubicin, doxorubicin, epirubicin, idarubicin, mitoxantrone, valrubicin and the like; taxane compounds, such as, for example, paclitaxel, docetaxel and the like; topoisomerase inhibitors such as, for example, etoposide, teniposide, tuliposide, irinotecan and the like; nucleotide analogs such as, for example, azacitidine, azathioprine, capecitabine, cytarabine, doxifluridine, fluorouracil, gemcitabine, mercaptopurine, methotrexate, thioguanine, ftorafur and the like; platinum-based agents such as, for example, carboplatin, cisplatin, oxaliplatin and the like; antineoplastic agents such as, for example, vincristine, leucovorin, lomustine, procarbazine and the like; hormone modulators such as, for example, tamoxifen, finasteride, 5-α-reductase inhibitors and the like; vinca alkaloids such as, for example, vinblastine, vincristine, vindesine, vinorelbine and the like. Suitable chemotherapy agents are described in more detail in the literature, such as in The Merck Index in CD-ROM, $13^{th}$ edition.

The pharmaceutical composition of the invention can be administered by any route suitable for the administration of antibody-containing formulations, such as, for example, subcutaneous, intraperitoneal, intravenous, intramuscular, etc.

Illustrative examples of pharmaceutical dosage forms administered can be in the form of, for example, sterile solutions, suspensions or lyophilized products, in the suitable dosage form; in this case, said pharmaceutical compositions will include the suitable excipients, such as buffers, reagents, etc. In any case, the excipients will be chosen according to the chosen pharmaceutical dosage form.

The person skilled in the art understands that the mutations in the nucleotide sequence of the gene encoding LIF giving rise to conservative substitutions of amino acids at non-critical positions for the functionality of the protein are evolutionarily neutral mutations that do not affect their overall structure global or functionality. Said variants fall within the scope of the present invention.

"Functionally equivalent" or "Functionally equivalent variant thereof" as used in this specification describes a molecule which has a functional relationship with the molecule which it is derived from (i.e. a derivative of which it is). More typically, it has both a functional and a structural relationship the molecule which it is derived from. Functional/structural relationship are to be understood as follows:

A. Functional relationship: A molecule with a functional relationship to LIF as used herein has an effect in the range of 50 to 200% compared with the effect of LIF, more preferably in the range of 80 to 120% compared with the effect of LIF, and most preferably in the range of 95 to 105%, such as essentially 100% that of LIF in an in vitro assay for LIF activity. Various in vitro assay for LIF activity are known to the skilled person. For example, differentiation of melanocytes upon addition of LIF or a functional equivalent thereof can be measured, as shown by Hirobe, 2002, J. Cell. Phys., 192:315-326. More particularly, the percentage of melanocytes upon addition of LIF can be determined, as shown in FIG. 2A of Hirobe, 2002, J. Cell. Phys., 192:315-326.

B. Structural Relationship: (1) the molecule may migrate in standard Tris/Glycine SDS Polyacrylamide gel electrophoresis, as known to the skilled person, essentially identical to LIF and/or it is a molecule having a different glycosylation pattern and/or it is a molecule the amino acid sequence of which is derived to human LIF, i.e. wherein one or more (i.e. 1 to 5, 1 to 10 or 1 to 20) amino acids of human LIF are modified, substituted, added or deleted. Those functionally equivalent variants of LIF having said insertions, deletions or modifications of one or more amino acids with respect to LIF and, furthermore conserve the same functions as LIF, are therefore also included within the scope of the invention. In a preferred embodiment, "Functionally equivalent" or "Functionally equivalent variant thereof" describes a molecule capable of carrying out essentially the same function as LIF. Therefore, as it is used herein the term "Functionally equivalent" or "Functionally equivalent variant thereof" also includes any functionally equivalent fragment of LIF. The same as described here for the functionally equivalent variant of LIF also applies for functionally equivalent variants of other proteins, such as CD44, Id1 and Id3.

The term "fragment" relates to a peptide comprising a portion of a protein. In this case, a functionally equivalent fragment of LIF is a peptide or protein comprising a portion of LIF and having essentially the same functions as LIF. The essentially same function of an effector, such as LIF, may be determined as described above under "A: functional relationship".

A "fragment of an antibody" is a peptide or a plurality of peptides (such as typically two, three of four peptides) comprising a portion of the antibody. These peptides optionally comprise intermolecular or intramolecular disulfide bridges. Hence, a fragment of an antibody may comprise one or two light chains or fragments thereof and/or one or two heavy chains or fragment(s) thereof, optionally linked by disulfide bridges. Combinations with one heavy and light chain or fragment(s) thereof or two heavy and two light chains or fragment(s) thereof are most typical. The relevant fragments of the antibody, or, more particularly, the fragments of the light chains and heavy chains, are preferably fragments which comprise the variable domains ($V_H$) of the antibody/chain, and more particularly comprise the antigen binding region of the antibody/chain.

Anti-LIF antibodies, preferably anti-LIF antibodies according to the present invention, are also potentially of interest for the treatment of tumors resistant to chemotherapy given the known capacity of tumor stem cells of being resistant to chemotherapy. In addition, the authors show that use of anti-LIF antibodies, preferably anti-LIF antibodies according to the present invention, is also suitable to prevent the occurrence of relapses in diseases associated with unwanted cell proliferation (FIG. 7).

Diagnostic Methods of the Invention

The authors of the present invention have found that LIF induces the cell proliferation process and the increase of tumor stem cells (cancer stem cells) by its involvement in the JAK/STAT cascade. More particular, the authors provide evidence that CD44 and Id1 are novel markers of glioma. Furthermore the authors showed that Id1 is preferentially expressed in a cell subpopulation enriched for GICs characterized by the expression of high levels of CD44 and that ID1 and ID3 are genes included in a signature of antibody-mediated LIF-inhibition. Therefore, LIF, CD44, Id1, Id3 or any combination thereof can be used in diagnostic methods for diagnosing diseases associated with unwanted cell proliferation. The diagnostic methods are based on determining the levels of LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules. Preferably, the diagnostic methods are based on determining the levels of LIF or of a functionally equivalent variant thereof.

Thus, in another aspect, the invention relates to an in vitro method for the diagnosis of diseases associated with unwanted cell proliferation in a subject or for determining the predisposition of a subject to suffer from said disease associated with unwanted cell proliferation, or for determining the stage or severity of said disease associated with unwanted cell proliferation in a subject, or for monitoring the effect of the therapy administered to a subject with said disease associated with unwanted cell proliferation, which comprises quantifying the expression levels of LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules in a biological sample from said subject, wherein an increase of the expression of the gene encoding LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules, with respect to the expression levels of the gene encoding LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules in a control sample, is indicative of a disease associated with unwanted cell proliferation, or of a greater predisposition of said subject to suffer from a disease associated with unwanted cell proliferation or of the non-response to the therapy administered to said subject. In a preferred embodiment, said in vitro method comprises quantifying the expression levels of the gene encoding LIF or a functionally equivalent variant thereof with respect to the expression levels of the gene encoding LIF or a functionally equivalent variant thereof in a control sample.

Therefore, as it is used herein the term "functionally equivalent variant" also includes any functionally equivalent fragment of said marker proteins. The term "fragment" relates to a peptide comprising a portion of said marker protein. In this case, a functionally equivalent fragment is a peptide or protein comprising a portion said marker protein and having essentially the same functions as said protein. "Marker protein" preferably refers to LIF, CD44, Id1 and Id3, without being limited thereto.

As used herein, diagnosing relates to evaluating the probability according to which a subject suffers from a disease. As will be understood by the persons skilled in the art, such evaluation normally may not be correct for 100% of the subjects to be diagnosed, although it is preferably is. However, the term requires being able to identify a statistically significant part of the subjects as suffering from the disease or having a predisposition to same. The person skilled in the art can determine if a part is statistically significant by simply using one or several well known statistical evaluation tools, for example, determination of confidence intervals, determination of the p-value, Student's t-test, Mann-Whitney test, etc. The details are in Dowdy and Wearden, Statistics for Research, John Wiley & Sons, New York 1983. The preferred confidence intervals are at least 50%, at least 60%, at least 70%, at least 80%, at least 90%, at least 95%. The p-values are preferably 0.2, 0.1, 0.05.

As used herein, the term "predisposition" means that a subject has still not developed the disease or any of the symptoms of the disease mentioned above or other diagnostic criteria but will, however, develop the disease in the future with a certain probability. Said probability will be significantly different from the statistical probability of onset of a disease associated with unwanted cell proliferation. It is preferably diagnosed that the probability of developing a disease associated with unwanted cell proliferation is at least 30%, at least 40%, at least 50%, at least 60%, at least 70%, at least 80%, at least 90% or 100% of a predisposition. The diagnosis of a predisposition can sometimes be referred to as prognosis or prediction of the probability of a subject developing the disease.

In the context of the present invention, "control sample" is understood as the reference sample which is used to determine the variation of the expression levels of the genes and proteins used in the present invention. In an embodiment, the reference value is obtained from the provided signal using a sample of tissue obtained from a healthy individual. Preferably, samples are taken from the same tissue of several healthy individuals and combined, such that the amount of polypeptides in the sample reflects the mean value of said molecules in the population.

Thus, in a particular embodiment of the invention, the expression levels of LIF or of CD44 or of Id1 or of Id3 can be quantified.

As is understood by the person skilled in the art, the expression level of a protein can be quantified by means of any conventional method. By way of non-limiting illustration, the levels of protein can be quantified, for example, by means of the use of antibodies with the capacity to bind to said proteins (or to fragments thereof containing an antigenic determinant) and the subsequent quantification of the complexes formed. The antibodies which are used in these assays may or may not be labeled. Illustrative examples of markers which can be used include radioactive isotopes, enzymes, fluorophores, chemiluminescent reagents, enzyme substrates or cofactors, enzyme inhibitors, particles, dyes, etc. There is a large variety of known assays which can be used in the present invention which use non-labeled antibodies (primary antibody) and labeled antibodies (secondary antibody); these techniques include Western-blot, ELISA (enzyme-linked immunosorbent assay), RIA (radioimmunoassay), competitive EIA (competitive enzyme immunoassay), DAS-ELISA (double-antibody sandwich ELISA), immunocytochemical and immunohistochemical techniques, techniques based on the use of biochips or microarrays of proteins which include specific antibodies or assays based on colloidal precipitation in formats such as dipsticks. In another particular embodiment, the quantification of the levels of protein is performed by means of an immoanalytical method, such as Western blot, immunohistochemistry or ELISA. In an even more particular embodiment, said immunoanalytical method comprises the antibody produced by the hybridoma cell line with the accession number DSM ACC3054 in the sense of this invention.

Likewise, the diagnostic method of the invention can be applied to any of the diseases associated with unwanted cell proliferation defined above. In a preferred embodiment, the disease associated with unwanted cell proliferation is a cancer, preferably a cancer having high levels of LIF or high levels of any of the following: Id1, Id3, CD44.

Putting the method of the invention into practice comprises obtaining a biological sample from the subject to be studied. Illustrative non-limiting examples of said samples include different types of biological fluids, such as blood, serum, plasma, cerebrospinal fluid, peritoneal fluid, faeces, urine and saliva, as well as samples of tissues. The samples of biological fluids can be obtained by any conventional method like the samples of tissues; by way of illustration said samples of tissues can be samples of biopsies obtained by surgical resection.

In another aspect, the invention relates to a kit comprising reagents for the quantification of the expression levels of LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules for the diagnosis of cancer in a subject or for determining the predisposition of a subject to suffer from said cancer, or for determining the stage or severity of said cancer in a subject, or for monitoring the effect of the therapy administered to a subject with said cancer, in which if the reagents detect an increase in the expression of said gene or said protein or functionally equivalent variant thereof with respect to a control sample, then said subject can suffer from a disease associated with unwanted cell proliferation, or present a greater predisposition to suffer from said disease associated with unwanted cell proliferation, or present a greater severity of said disease, or the administered therapy is not being effective. In a preferred embodiment thereof, the kit is characterized by comprising reagents for the quantification of the expression levels of LIF or of a functionally equivalent variant thereof.

The invention also relates to the use of said kit.

All the terms and expressions used in the definition of the use of the kit have been described above and explained for other inventive aspects and particular embodiments of the present invention, and are also applicable to the use of the kit described herein.

Methods for Designing Customized Therapies and for Selecting Patients Who can Benefit from the Therapy Based on the Anti-LIF Antibody In another aspect, the invention relates to an in vitro method for designing a customized therapy for a patient suffering from a disease associated with unwanted cell proliferation comprising:

(a) quantifying the expression levels of LIF in said patient, and (b) comparing said expression levels with control levels, wherein if the expression levels of LIF in said patient are greater than the control values, then an antibody directed against LIF is administered to said patient.

In another aspect, the invention relates to an in vitro method for selecting patients suffering from a disease associated with unwanted cell proliferation, to be treated with an antibody directed against LIF comprising a) quantifying the expression levels of LIF in said patient, and b) comparing said expression levels with control levels, wherein if the expression levels of LIF in said patient are greater than the control values, then said patient is selected to receive treatment with an antibody directed against LIF.

In both aspects, a preferred embodiment is that in which the disease associated with unwanted cell proliferation is associated with unwanted stem cell proliferation.

The diseases presenting unwanted cell proliferation are those described above. In a preferred embodiment, said disease presenting unwanted cell proliferation is cancer. Even more preferably, said cancer is caused by a high activity of the JAK-STAT signaling pathway.

In a preferred embodiment, said cancer is one of the following: glioma, pre-B cell acute lymphoblastic leukemia, acute myeloid leukemia, colorectal carcinoma, lung adeonocarcinoma, prostate adenocarcinoma, bladder cancer, breast ductal cancer or breast carcinoma. Even more preferably, said glioma is grade IV glioma.

Prognostic Methods of the Invention

In another aspect, the invention relates to a prognostic in vitro method for predicting the average life expectancy of patients suffering from a disease associated with unwanted cell proliferation. This method is based on the observation that, e.g. in case of glioma, the average life expectancy is reduced for patients showing higher LIF expression levels than control patients. The authors provide evidence that CD44 and Id1 are markers of GICs. These markers confer poor prognosis in GBM patients. The above-specified connection between higher levels of LIF and higher levels of Id1 and CD44, respectively, in subjects suffering from a disease associated with unwanted cell proliferation, provides novel markers on which prognostic methods can rely.

The method is based on
a) quantifying the expression levels of LIF or of CD44 or of Id1 or of Id3 in said patient, and
b) comparing said expression levels with control levels,
wherein if the expression levels of LIF or of CD44 or of Id1 or of Id3 in said patient are greater than the values of control patients of that same disease, then said patient likely has a lower life expectancy than the control group.

In a more specific aspect, the concentration of LIF or of CD44 or of Id1 or of Id3 or of a functionally equivalent variant of any of these markers can be measured for prognostic purposes, namely for the prediction of average life expectancy of an individual suffering from said disease. Preferably, the concentration o LIF or functionally equivalent variant thereof is measured. For this purpose, the concentration of LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules from the tumor patient are compared to the reference concentration of that same marker. As used herein, LIF, CD44, Id1 and Id3 or functionally equivalents of LIF, CD44, Id1 and Id3 are "markers". Preferably, the concentration of LIF or of a functionally equivalent variant thereof from the tumor patient is compared to the reference concentration of LIF or of a functionally equivalent variant thereof, i.e. the marker being LIF or a functionally equivalent variant thereof. The reference sample is taken from a reference patient group. The group of reference patients typically consists of patients who are well documented and who suffer from the same disease. For example, the reference sample can be obtained from identical amounts of a group of at least 2, at least 10, at least 100 to more than 1000 individuals, such that the population of patients suffering from said disease is statistically significant. The reference group can consist of one or more of the following:
a) all patients suffering from said disease
b) all patients suffering from said disease who do not show significantly upregulated levels of LIF
c) all patients suffering from said disease who show significantly downregulated levels of LIF.

The concentration of LIF can be determined intracellular, in the interstitial gap or in extracts in which both the intracellular protein and the one found in the interstitial gap.

In this aspect, a preferred embodiment is a disease associated with unwanted cell proliferation. In a more particular embodiment, the disease associated with unwanted cell proliferation is cancer. Even more preferred, the type of cancer is associated with abnormally high levels of LIF in a subset of patients of said cancer. In a more particular embodiment, the cancer is one of the following: leukemia, glioma, colorectal carcinoma, bladder cancer, breast cancer. In a more particular embodiment, the leukemia is pre-B cell acute lymphoblastic leukemia or acute myeloid leukemia and the breast cancer is breast ductal cancer or breast carcinoma.

Statistical methods will allow for predicting average life expectancy of patients based on the levels of said protein or functionally equivalent variants thereof. Said protein is preferably LIF.

As used herein the term "functionally equivalent variant" also includes any functionally equivalent fragment of said marker proteins LIF. The term "fragment" relates to a peptide comprising a portion of said marker protein. In this case, a functionally equivalent fragment is a peptide or protein comprising a portion said marker protein and having essentially the same functions as said protein.

In a more particular embodiment, the quantification of the levels of protein is performed by means of an immoanalytical method, such as Western blot, immunohistochemistry or ELISA. In an even more particular embodiment, said immunoanalytical method comprises the antibody produced by the hybridoma cell line with the accession number DSM ACC3054.

EXAMPLES

The invention is described below by means of the following examples which must be considered as merely illustrative and non-limiting examples thereof.

Materials and Methods:

Cell Lines and Primary Cell Cultures

PCTCs and GBM neurospheres were generated as described previously (Bruna et al., Cancer Cell, 11:147-160, 2007; Gunther et al., Oncogene, 2007). Briefly, tumor samples were processed within 30 min after surgical resection. Minced pieces of human GBM samples were digested with 200 U/ml collagenase I (Sigma) and 500 U/ml DNase I (Sigma) in PBS for 2 hr at 37° C. with constant vigorous agitation. The single-cell suspension was filtered through a 70 μm cell strainer (BD Falcon) and washed with PBS. Finally, cells were resuspended and subsequently cultured in DMEM with 10% FBS (for PCTC culture) or in neurosphere medium (for GBM neurospheres). The neurospheres medium consisted of Neurobasal medium (GIBCO) supplemented with B27 (GIBCO), Lglutamine (GIBCO), penicillin/streptomycin, and growth factors (20 ng/ml EGF and 20 ng/ml FGF-2 [PeproTech]). Human GBM specimens were obtained from the Vall d'Hebron Hospital.

The clinical protocol was approved by the Vall d'Hebron Institutional Review Board (CEIC), with informed consent obtained from all subjects. Intracranial Tumor Assay All mouse experiments were approved by and performed according to the guidelines of the Institutional Animal Care Committee of the Vall d'Hebron Research Institute in agreement with the European Union and national directives. The cells were stereotactically inoculated into the corpus striatum of the right brain hemisphere (1 mm anterior and 1.8 mm lateral to the bregma; 2.5 mm intraparenchymal) of 9-weekold NOD/SCID mice (Charles River Laboratories). Mice were euthanized when they presented neurological symptoms or a significant loss of weight. Magnetic resonance imaging (MRI) analysis was performed in mice injected intraperitoneally with gadolinium diethylenetriamine penta-acetic acid at a dose of 0.25 mmol gadolinium/kg body weight. T1W magnetic resonance images from the entire brain were acquired in a 9.4 T vertical bore magnet interfaced to an AVANCE 400 system (Bruker) using a spin-echo sequence as described previously (Penuelas et al., Cancer Cell, 15:315-327, 2009). Tumor volume was quantified by measuring the number of pixels corresponding to tumor tissue in each image using the software provided by the manufacturer (Bruker).

Statistical Analysis

A Student t-test was performed for statistical analysis. Data in graphs are presented as mean±SD.

Plasmids and Reagents

TGFβ1 (R&D), TPR1 inhibitor LY2109761 (Eli Lilly) and SB431542 (Tocris) were used at the indicated concentrations. Specific antibodies against p-Smad2, Smad2 (Cell Signaling); α-Tubulin (Sigma) and Id1 (C20, Santa Cruz Biotechnology) were used for immunoblotting. Lentiviral constructs were produced and packaged as previously described (Zufferey et al., Nat. Biotechnol., 15:871-875, 1997). Neurospheres were dissociated in growth media, mixed with virus and plated. Polybrene (Sigma) was added at a concentration of 8 µg/ml. Cells were incubated with virus for 12 hours, washed with PBS, and incubated in fresh media as previously described (Zufferey et al., Nat. Biotechnol., 15:871-875, 1997).

Analysis of the CD44-Positive Population by Flow Cytometry Neurospheres were dissociated and individual cells were incubated for 15 min in blocking solution containing 10 µg/ml human IgG, followed by anti-CD44 antibody or the control IgG2b isotype, both FITC-conjugated (BD Pharmingen). Cells were incubated for 20 min on ice protected from light, washed in PBS and stained with Propidium Iodide (Sigma) to discriminate dying cells. Cells were then analyzed by flow cytometry (FACSCalibur; Beckton Dickinson) or sorted (MoFlo; DAKO) after staining with CD44-FITC.

Isolation of Human Cells from Orthotopic Xenografts in Mouse Brains

Brains from mice inoculated with neurospheres were dissociated and stained with the pan-MHC class I specific mAb HP-1F7 (Santa Cruz Biotechnology) followed by secondary PE-conjugated mAb (Dako Cytomation) for subsequent cell sorting of human MHC-I positive cells (MoFlo-DAKO). Cells obtained were washed and immediately used in subsequent experiments.

Neurosphere-Forming Assay

Equal number of cells was seeded at low cell density (4 cells/µl) in wells of a 96-well plate. Cells were treated with the indicated compounds and the total number of newly formed neurospheres was counted after 7 days in culture (Lee, et al. Cancer Cell, 13:69-80, 2008; Reynolds and Weiss, Dev. Biol. 175:1-13, 1996)

Self-Renewal Assay

Cells from the indicated GBM neurospheres plated at 100 cells/µl were treated with the indicated compounds for 7 days. Neurospheres were then dissociated, re-plated in the absence of treatment and incubated for another 7 days. The total number of newly formed neurospheres was counted.

Quantitative Real-Time PCR

Quantitative Real-Time PCR (qRT-PCR) was performed using Taqman probes from Applied Biosystems, according to the manufacturer's recommendations. Reactions were carried out in an ABI 7900 sequence detector (Perkin Elmer) and results were expressed as fold change calculated by the ΔΔCt method relative to the control sample. GAPDH was used as an internal normalization control.

Immunohistochemistry, Immunocytochemistry

For tissue microarray generation, three 0.6 mm cores were taken from separate areas, and each one was arrayed into recipient blocks in a 1 mm-spaced grid. The following antibodies were used for the detection of proteins: anti-Id1 (BioCheck), anti-CD44 (Ab-4, Neomarkers), anti-CD31 (clone JC70A, DAKO). For quantitative analysis of Id1, the percentage of stained tumor cells and intensity of staining was evaluated in representative high-power fields (×400) on tissue sections using optical microscopy. The results were expressed as H-Score or percentage of positive cells.

Id1 (Santa Cruz Biotechnology) immunocytochemistry of neurospheres was performed as previously described in (Geschwind et al., Neuron, 29:325-329, 2001). Nuclei were counterstained with 4',6-diamidino-2-phenylindole (DAPI).

Microdisection

Areas of representative tumor, away from necrotic foci, were identified on 10 µm hematoxylineosin-stained sections of frozen samples. Tumor cells were microdisected using the Microdisector Leica LMD6000 and processed to obtain RNA using the RNAeasy Micro Kit (Qiagen) according to the manufacturer's recommendations.

Luciferase Assay

GBM neurosphere cells were transiently transfected with different ID1 promoter reporter constructs and pRL-TK Renilla luciferase plasmid (Promega) as a normalization control using Lipofectamine 2000 (Invitrogen).

Example 1

Hybridoma Cell Line Producing Antibodies Directed Against Human LIF

Hybridoma cell lines were generated for the purpose of production of antibodies directed against human LIF by methods well known to any person skilled in the art. From these hybridoma cell lines, one cell line was selected and deposited on Apr. 1, 2010 by Vall d'Hebron Institute of Oncology at the Deutsche Sammlung von Mikroorganismen und Zellkulturen GmbH. It was assigned the accession number DSM ACC3054. In accordance, also the homogenous population of antibodies produced by said cell line was selected. The binding specificity of anti-human LIF monoclonal antibodies (α-LIF) produced by the hybridoma cell line DSM ACC3054, deposited on Apr. 1, 2010 by Vall d'Hebron Institute of Oncology at the Deutsche Sammlung von Mikroorganismen und Zellkulturen GmbH, was subsequently determined by immunoprecipitation. To that end, 293T cells that had been transfected with C-terminally EGFP-tagged versions of the human LIF protein (FIG. 1A) were lysed and subjected to immunoprecipitation with the monoclonal anti-LIF antibody, followed by addition of protein A/G to the lysates and elution of immunoprecipitates. LIF fragments were detected by immunoblot using an anti-EGFP antibody. This analysis revealed that said antibody recognizes LIF and variants thereof, provided the C-terminal domain of the human LIF protein comprised by amino acids 160 to 202 is present. EGFP-tagged full-length LIF, but not EGFP-tagged LIF fragments corresponding to amino acids 1 to 72, 1 to 127 or 1 to 160 were recognized by the monoclonal antibody (FIG. 1B). Hence, the C-terminal domain of the human LIF protein comprised by amino acids 160 to 202 is required for recognition by the anti-LIF antibody (FIG. 1C).

Example 2

The Monoclonal Anti-LIF Antibody Blocks the Induction of Phospho-Stat3 by LIF in Cell Culture and in Patient-Derived Glioblastoma Neurospheres To test the effect of the monoclonal anti-LIF antibody produced by hybridoma cell line deposited on Apr. 1, 2010 by Vall d'Hebron Institute of Oncology at the Deutsche Sammlung von Mikroorganismen and Zellkulturen GmbH for its effectiveness in blocking effects downstream of LIF, U373 cells were treated with or without human recombinant LIF in the presence or absence of the indicated monoclonal antibody, or in the presence of an isotype-matched IgG as control. Subsequent determination of Phospho-Stat3 levels by Western Blot showed that the LIF-mediated induction of Phospho-Stat3 can effectively be blocked by administration of the monoclonal anti-LIF antibody (FIG. 2A).

To test the effect of said antibody on patient-derived cancer cells, patient derived GBM neurospheres were desegregated and optionally incubated in the presence of said antibody or isotype-matched control IgG. Subsequent determination of Phospho-Stat3 levels by Western Blot showed that the LIF-mediated induction of Phospho-Stat3 can effectively be blocked by administration of the monoclonal anti-LIF antibody in the patient-derived cells (FIG. 2B).

Example 3

Patient-Derived GBM Neurospheres Contain a $CD44^{high}/Id1^{high}$ Cell Compartment CD44 is a protein described to be highly expressed in CICs of certain tumors (Visvader and Lindeman, Nat. Rev. Cancer, 8:755-768, 2008). In accordance, the authors of the present study observed that in GBM neurospheres two discrete populations expressing different levels of CD44 are present (FIG. 3A). However, the $CD44^{high}$ compartment has so far not been extensively studied in glioma. In order to test whether the expression of CD44 is correlated to the expression of Id1 in cells derived from patient neurospheres, the $CD44^{high}$ population of neurospheres from four different patients was sorted by flow cytometry upon staining of cells as described in "Material and Methods". Subsequently, Id1 expression levels were determined in the $CD44^{high}$ and the $CD44^{low}$ populations, respectively. Interestingly, Id1 protein and RNA were detected at much higher levels in the $CD44^{high}$ than in the $CD44^{low}$ compartment (FIGS. 3B and 3C). Interestingly, Id3 was also present at higher levels in the $CD44^{high}$ population, however this was not the case for Id2, another member of the Id family of transcription factors (FIG. 3B). Hence, high levels of CD44 are correlated to high levels of Id1 and of Id3.

Example 4

The $CD44^{high}/Id1^{high}$ Population in GBM Neurospheres is Enriched for Glioma-Initiating Cells The authors observed that upon induction of differentiation of patient-derived neurospheres through the treatment with serum, the $CD44^{high}$ compartment disappeared (FIG. 4A). Next, the $CD44^{high}$ and $CD44^{low}$ cells were sorted and plated at low density. $CD44^{high}$ cells generated more neurospheres than the $CD44^{low}$ compartment (FIG. 4B) indicating that the $CD44^{high}$ cells had a higher neurosphere-forming capacity than the $CD44^{low}$ cells. Next, the tumor initiating capacity of the $CD44^{high}$ compared to the $CD44^{low}$ compartment was analyzed. Tumor cells were sorted based on the expression of CD44 and we performed in vivo limiting dilutions implanting decreasing amounts of cells in the right striatum of NOD-SCID mice. Tumor progression was monitored by magnetic resonance imaging (MRI). Cells expressing high levels of CD44 were much more tumorigenic than the CD44low expressing cells. Only 1 out of 7 mice inoculated with 100.000 $CD44^{low}$ cells developed tumors whereas 9 out of 9 mice generated tumors when they were inoculated with the same number of $CD44^{high}$ cells (FIGS. 4C and 4D). Moreover, mice inoculated with 10.000 or 1.000 $CD44^{high}$ cells generated tumors whereas the same number of $CD44^{low}$ never generated tumors. A similar result was obtained with cells from another patient, GBM2 (FIG. 4D). Tumors generated by the $CD44^{high}$ compartment reproduced the histopathological characteristics of the tumor of the patient including the same cellular heterogeneity (FIG. 4E). For example, tumors generated in the mouse contained the same percentage (around 70%) of Sox2 positive and negative cells than the tumor of the patient (FIG. 4E). All the results indicated that the $CD44^{high}$ compartment was enriched for GICs as has been shown in other tumor types.

Example 5

Anti-LIF Antibody Decreases the Levels of the $CD44^{high}/Id1^{high}$ Population in GBM Neurospheres GBM neurospheres were dissociated and cultured in the presence of anti-LIF monoclonal antibody from cell line DSM ACC3054 or isotype-matched control IgG for 7 days either in the presence (A) or absence (B) of EGF and FGF. Remarkably, neurospheres treated with the anti-LIF antibody decreased the $CD44^{high}$ compartment. Hence, TGFβ regulates the $CD44^{high}$ compartment which expresses high levels of Id1 and is enriched for GICs.

Example 6

Anti-LIF Antibody Decreases the Levels of the CD44 and Id1 in Patient-Derived GBM Neurospheres GBM neurospheres were dissociated and cultured in the presence of anti-LIF monoclonal antibody or isotype control IgG for 7 days in the absence of EGF and FGF and mRNA levels of the indicated genes were analysed by qRT-PCR. In comparison to isotype-matched control IgG, Id1 mRNA levels, as well as CD44 mRNA levels were significantly reduced upon application of the anti-LIF antibody in patient-derived GBM neurpspheres.

Example 7

In Vivo Treatment with Anti-LIF Antibody Decreases the $CD44^{high}/Id1^{high}$ Cell Compartment In order to assess if the decrease of the GIC population in tumors in response to application of the monoclonal anti-LIF antibody affects tumor relapse, the authors of the present invention first generated tumors in mice through the inoculation of GBM1 neurospheres. One month after inoculation of cells, mice were bearing tumors that were detected by MRI. At that point, mice were treated with the monoclonal anti-LIG antibody or isotype-matched IgG for 10 days and sacrificed. Human tumoral cells were isolated from the mouse brain through sorting of human MHC-I positive cells (FIG. 7A). Cells obtained from mice that were treated with the TβRI inhibitor showed lower levels of ID1, ID3 and CD44 transcripts as measured by qRT-PCR (FIG. 7B).

Example 8

Patients with Glioma or Glioblastoma Showing Upregulated LIF Levels have a Shorter Overall Life Expectancy In a subset of all glioma patients, LIF levels are upregulated ≥2 fold. Over a set period of time, those patients have a significantly reduced probability of survival compared to control patients. For example, the probability of survival after 1000 days is reduced to approximately 50% compared with all glioma patients, and to approximately 35% compared to glioma patients with LIF levels not upregulated ≥2 fold (FIG. 8). Data obtained from REpository for Molecular BRAin Neoplasia DaTa (REMBRANDT) program form the National Cancer Institute.

In a subset of all glioblastoma patients, LIF levels are upregulated ≥9 fold. Over a set period of time, those patients have a significantly reduced probability of survival compared to control patients. For example, the probability of survival after 500 days is reduced to approximately 50% compared with all glioblastoma patients (FIG. 9). Data obtained from REpository for Molecular BRAin Neoplasia DaTa (REMBRANDT) program form the National Cancer Institute.

Preferred Embodiments of the Invention

The following are preferred embodiments of this invention. The invention should however not be understood as being limited to these preferred embodiments:

1. A monoclonal antibody or a fragment thereof, which recognizes full length human LIF, but does not recognize a LIF fragment corresponding to amino acids 1 to 72, and more preferably, does not recognize a LIF fragment corresponding to amino acids 1 to 127, and even more preferably, does not recognize a LIF fragment corresponding to amino acids 1 to 160.

2. The monoclonal antibody of embodiment 1 wherein said antibody recognizes an epitope of human LIF comprised in the region corresponding to amino acids 160 to 202 of human LIF.

3. The monoclonal antibody of embodiment 1 wherein said antibody recognizes an epitope comprised in the regions selected from the following: a region corresponding to amino acids 160 to 180, a region corresponding to amino acids 170 to 190, a region corresponding to amino acids 180 to 200, a region corresponding to amino acids 182 to 202 of human LIF.

4. The monoclonal antibody according to any one of the preceeding embodiments wherein the antibody is competitively inhibited in its binding to human LIF by the monoclonal antibody produced by a hybridoma deposited on Apr. 1, 2010 by Vall d'Hebron Institute of Oncology at the Deutsche Sammlung von Mikroorganismen and Zellkulturen GmbH.

5. The monoclonal antibody according to any one of the preceeding embodiments of the IgG1 isotype.

6. The monoclonal antibody according to any of the preceeding embodiments, which is produced by the hybridoma cell line with the accession number DSM ACC3054, deposited on Apr. 1, 2010 by Vall d'Hebron Institute of Oncology at the Deutsche Sammlung von Mikroorganismen und Zellkulturen GmbH.

7. A hybridoma deposited on Apr. 1, 2010 by Vall d'Hebron Institute of Oncology at the Deutsche Sammlung von Mikroorganismen und Zellkulturen GmbH.

8. An immunoanalytical reagent used in the measurement of human LIF, which comprises the monoclonal antibody or fragment thereof according to any one of embodiments 1 to 6.

9. The monoclonal antibody or fragment thereof according to any one of embodiments 1 to 6, wherein said antibody or fragment thereof acts through the inhibition of the self-regeneration of tumor stem cells.

10. An antibody or fragment thereof directed against human LIF for treatment of a disease associated with unwanted cell proliferation.

11. The antibody or fragment thereof according to any of embodiments 1 to 6 or 9 for treatment of a disease associated with unwanted cell proliferation.

12. A pharmaceutical composition comprising a therapeutically effective amount of an antibody or fragment thereof according to any one of the embodiments 1 to 6 or 9 to 11 together with a pharmaceutically acceptable carrier.

13. In vitro method for the diagnosis of diseases associated with unwanted cell proliferation in a subject or for determining the predisposition of a subject to suffer from said disease associated with unwanted cell proliferation, or for determining the stage or severity of said disease associated with unwanted cell proliferation in a subject, or for monitoring the effect of the therapy administered to a subject with said disease associated with unwanted cell proliferation, which comprises quantifying the expression levels of LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules in a biological sample from said subject, wherein an increase of the expression of the gene encoding LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules, with respect to the expression of the gene encoding LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules in a control sample, is indicative of a disease associated with unwanted cell proliferation, or of greater predisposition of said subject to suffer from a disease associated with unwanted cell proliferation or of the nonresponse to the therapy administered to said subject.

14. The use of a kit comprising reagents for the quantification of the expression levels of LIF or of a functionally equivalent variant thereof, or of CD44 or of a functionally equivalent variant thereof, or of Id1 or of a functionally equivalent variant thereof, or of Id3 or of a functionally equivalent variant thereof or of any combination of these molecules for the diagnosis of a disease associated with unwanted cell proliferation in a subject or for determining the predisposition of a subject to suffer from said disease, or for determining the stage or severity of said disease in a subject, or for monitoring the effect of the therapy administered to a subject with said disease, wherein if the reagents detect an increase in the expression of said gene or said protein or functionally equivalent variant thereof with respect to a control sample, then said subject can suffer from said disease, or present a greater predisposition to suffer from said disease, or present a greater severity of said disease, or the administered therapy is not being effective.

15. An in vitro method for designing a customized therapy for a patient suffering from a disease associated with increased LIF levels comprising:
(a) quantifying the expression levels of LIF in said patient, and
(b) comparing said expression levels with control levels, wherein if the expression levels of LIF in said patient are greater than the control values, then an antibody of LIF is administered to said patient.

16. An in vitro method for selecting patients suffering from a disease associated with unwanted cell proliferation, to be treated with an antibody directed against LIF comprising
(a) quantifying the expression levels of LIF in said patient, and
(b) comparing said expression levels with control levels, wherein if the expression levels of LIF in said patient are greater than the control values, then said patient is selected to receive treatment with the antibody according to embodiments 1 to 6 or 9 to 12 or fragment thereof.

17. An in vitro method for the prognosis of life expectancy or of the probability of survival of subjects suffering from diseases associated with unwanted cell proliferation, comprising quantification of the expression levels of LIF or a functionally equivalent thereof in a biological sample from said subject, wherein an increase of LIF expression or functionally equivalent thereof, with respect to LIF expression or functionally equivalent thereof in a control sample, is indicative of a reduced life expectancy.

18. The antibody or fragment thereof or the pharmaceutical composition, or the method or the kit according to any of embodiments 10 to 14, wherein said disease presenting unwanted cell proliferation is characterized by presenting high levels of LIF.

19. The antibody or fragment thereof or the pharmaceutical composition, or the method or the kit according to any of the embodiments 10 or 17, wherein said disease presenting unwanted cell proliferation is characterized by a cell population expressing high levels of CD44 and Id1.

20. The antibody or fragment thereof or the pharmaceutical composition, or the method or the kit according to any of embodiments 10 to 19, wherein said disease presenting unwanted cell proliferation is cancer.

21. The antibody or fragment thereof or the pharmaceutical composition, or the method or the kit according to any of the embodiments 18 to 20, wherein said cancer is one of the following: glioma, pre-B cell acute lymphoblastic leukemia, acute myeloid leukemia, lung adenocarcinoma, prostate adenocarcinoma, colorectal carcinoma, bladder cancer, breast ductal cancer or breast carcinoma.

22. The antibody or fragment thereof or the pharmaceutical composition, or the method or the kit according to embodiment 21, wherein said glioma is grade IV glioma.

23. The method or kit according to any of embodiments 13 to 22, wherein the quantification of the levels of LIF is performed by means of Western blot, immunohistochemistry or ELISA.

24. The method or kit according to any of the embodiments 13 to 23 wherein the method or kit for measuring the expression levels of LIF comprises the monoclonal antibody according to embodiments 1 to 6 or 9 or fragment thereof.

25. The antibody or fragment thereof or pharmaceutical composition according to any of the embodiments 1 to 6, or 9 to 12 or 20 to 22, wherein said antibody or fragment thereof is capable of reducing the cell population characterized by high levels of CD 44 and Id1.

26. The antibody or fragment thereof or pharmaceutical composition according to any of the embodiments 1 to 6, 9 to or 20 to 22, wherein said antibody acts through the inhibition of the self-regeneration of tumor stem cells.

27. The antibody or fragment thereof or pharmaceutical composition or kit or method of any of the preceding embodiments, wherein the term "LIF or a functionally equivalent variant thereof, or CD44 or of a functionally equivalent variant thereof, or Id1 or of a functionally equivalent variant thereof, or Id3 or of a functionally equivalent variant thereof" is limited to LIF or a functionally equivalent variant thereof.

The invention claimed is:

1. A monoclonal antibody or a fragment thereof, which binds full length human Leukemia inhibitory factor (LIF), but does not bind a LIF fragment corresponding to amino acids 1 to 160, wherein the full length human LIF is the precursor to human LIF isoform 1.

2. The monoclonal antibody of claim 1, wherein said antibody binds an epitope of human LIF comprised in the region corresponding to amino acids 160 to 202 of human LIF.

3. The monoclonal antibody of claim 1, wherein said antibody binds an epitope comprised in the regions selected from the following: a region corresponding to amino acids 160 to 180, a region corresponding to amino acids 170 to 190, a region corresponding to amino acids 180 to 200, a region corresponding to amino acids 182 to 202 of human LIF.

4. The monoclonal antibody according to claim 1, wherein the antibody is competitively inhibited in its binding to human LIF by the monoclonal antibody produced by a hybridoma deposited on Apr. 1, 2010 by Vall d'Hebron Institute of Oncology at the Deutsche Sammlung von Mikroorganismen and Zellkulturen GmbH (deposit number DSM ACC3054).

5. The monoclonal antibody according to claim 1 of the IgG 1 isotype.

6. The antibody of claim 1, wherein the antibody is a humanized antibody.

7. The monoclonal antibody according to claim 1, which is produced by the hybridoma cell line deposit number DSM ACC3054, deposited on Apr. 1, 2010 by Vall d'Hebron Institute of Oncology at the Deutsche Sammlung von Mikroorganismen und Zellkulturen GmbH.

8. A pharmaceutical composition comprising a therapeutically effective amount of an antibody or fragment thereof according to claim 1 together with a pharmaceutically acceptable carrier.

9. An immunoanalytical reagent comprising the monoclonal antibody or fragment thereof according to claim 1, for the measurement of human LIF.

10. The hybridoma cell line deposit number DSM ACC3054, deposited on Apr. 1, 2010 by Vall d'Hebron Institute of Oncology at the Deutsche Sammlung von Mikroorganismen und Zellkulturen GmbH.

* * * * *